US010463791B2

(12) United States Patent
Shergold et al.

(10) Patent No.: US 10,463,791 B2
(45) Date of Patent: Nov. 5, 2019

(54) HAND-HELD INJECTION DEVICES AND METHODS OF USE

(71) Applicant: Roche Diagnostics Operations, Inc., Indianapolis, IN (US)

(72) Inventors: Oliver Shergold, Bolligen (CH); Simon Scheurer, Bern (CH)

(*) Notice: Subject to any disclaimer, the term of this patent is extended or adjusted under 35 U.S.C. 154(b) by 9 days.

(21) Appl. No.: 14/189,139

(22) Filed: Feb. 25, 2014

(65) Prior Publication Data

US 2015/0057616 A1 Feb. 26, 2015

Related U.S. Application Data

(63) Continuation of application No. PCT/EP2011/004467, filed on Sep. 5, 2011.

(51) Int. Cl.
| | |
|---|---|
| *A61M 5/19* | (2006.01) |
| *A61M 5/168* | (2006.01) |
| *A61M 5/20* | (2006.01) |
| *A61M 5/24* | (2006.01) |
| *A61B 5/15* | (2006.01) |

(Continued)

(52) U.S. Cl.
CPC .............. *A61M 5/19* (2013.01); *A61B 5/157* (2013.01); *A61B 5/150022* (2013.01); *A61M 5/14216* (2013.01); *A61M 5/16809* (2013.01); *A61M 5/20* (2013.01); *A61M 5/204* (2013.01); *A61M 5/24* (2013.01); *A61M 5/31548* (2013.01); *A61M 5/31593* (2013.01); *A61M 5/34* (2013.01); *A61B 5/150358* (2013.01); *A61M 5/1723* (2013.01); *A61M 2005/14268* (2013.01); *A61M 2005/1587* (2013.01);

(Continued)

(58) Field of Classification Search
CPC .. A61M 5/14216; A61M 5/1422; A61M 5/19; A61M 5/31553; A61M 5/16881
USPC ........................................................ 604/191
See application file for complete search history.

(56) References Cited

U.S. PATENT DOCUMENTS 3,718,409 A * 2/1973 Brandenberg ........ F01L 25/063
417/326
4,065,230 A * 12/1977 Gezari ................ A61M 5/1422
417/317

(Continued)

FOREIGN PATENT DOCUMENTS

| EP | 2062527 A1 | 5/2009 |
|---|---|---|
| EP | 2163273 A1 | 3/2010 |

(Continued)

*Primary Examiner* — Edelmira Bosques

(57) ABSTRACT

At least one hand-held injection device for the metered injection of a liquid drug into a person's tissue is disclosed. The exemplary injection device comprises an elongated drug reservoir having a longitudinal reservoir axis (A), an elongated dosing unit having a dosing unit inlet, a dosing unit outlet, and a metering cavity, the dosing unit having a longitudinal dosing unit axis (A'), the elongated drug reservoir being fluidically coupled to the dosing unit inlet. The dosing unit and the drug reservoir are arranged such that the longitudinal dosing unit axis (A') is in parallel alignment with the reservoir axis (A). The dosing unit structured to allow the flow of the liquid drug from the drug reservoir into the metering cavity via the dosing unit inlet, thus charging the metering cavity, and to subsequently discharge the metering cavity by dosing drug out of the metering cavity into the dosing unit outlet.

19 Claims, 11 Drawing Sheets

(51) Int. Cl.
*A61B 5/157* (2006.01)
*A61M 5/315* (2006.01)
*A61M 5/34* (2006.01)
*A61M 5/142* (2006.01)
*A61M 5/172* (2006.01)
*A61M 5/158* (2006.01)
*A61M 5/31* (2006.01)

(52) U.S. Cl.
CPC ............... *A61M 2005/3128* (2013.01); *A61M 2205/3327* (2013.01); *A61M 2205/3561* (2013.01); *A61M 2205/52* (2013.01)

(56) References Cited

U.S. PATENT DOCUMENTS

| | | | | |
|---|---|---|---|---|
| 5,046,496 | A * | 9/1991 | Betts | G01N 33/4925 204/403.03 |
| 5,876,380 | A * | 3/1999 | Manganini | A61M 5/001 604/191 |
| 6,423,035 | B1 * | 7/2002 | Das | A61M 5/1456 128/DIG. 1 |
| 7,338,472 | B2 * | 3/2008 | Shearn | A61M 5/1456 604/155 |
| 2003/0014013 | A1 * | 1/2003 | Choi | A61M 5/14244 604/154 |
| 2005/0137659 | A1 * | 6/2005 | Garabedian | A61B 18/148 607/96 |
| 2005/0177111 | A1 * | 8/2005 | Ozeri | A61M 5/1456 604/154 |
| 2008/0077081 | A1 | 3/2008 | Mounce et al. | |
| 2009/0216194 | A1 * | 8/2009 | Elgard Pedersen | A61M 5/14248 604/151 |
| 2010/0256593 | A1 * | 10/2010 | Yodfat | A61M 5/14248 604/504 |

FOREIGN PATENT DOCUMENTS

| | | |
|---|---|---|
| EP | 2283885 A1 | 2/2011 |
| WO | 2004108193 A1 | 12/2004 |
| WO | 2011010198 A2 | 1/2011 |
| WO | 2011032960 A1 | 3/2011 |

* cited by examiner

HAND-HELD INJECTION DEVICES AND METHODS OF USE

CROSS REFERENCE TO RELATED APPLICATIONS

This application is a continuation of International Application No. PCT/EP2011/004467 filed Sep. 5, 2011, the contents of which are hereby incorporated by reference in their entirety into this disclosure.

TECHNICAL FIELD

The present disclosure is directed towards hand-held injection devices for the metered injection of a liquid drug into a person's tissue, to injection device kits and to disposable modules that may be used in or in combination with hand-held injection devices as well as to the use of disposable modules in injection devices and injection device kits.

BACKGROUND

Hand-held injection devices are widely used for the self-injection of liquid drugs in a number of therapies. They are, for example, commonly used for the self-injection of liquid insulin formulations by diabetics, for the injection of growth hormones and a variety of further therapies. In the following, reference is mainly made to the self-injection of liquid insulin formulations as an exemplary field of application. Devices, methods, and kits in accordance with the present disclosure are therefore generally designed to be applied in diabetes therapy, without excluding further applications. Injection devices in accordance with the present disclosure are designed to administer the total volume of drug that is held by a drug reservoir in a number of single injections over an extended time period of typically several days up to several weeks.

In the context of the present disclose, the phrase "injection device" refers to a device that is designed for carrying out injections, an injection including the steps of temporarily fluidically coupling the injection device to a person's tissue, typically the subcutaneous tissue. An injection further includes administering an amount of liquid drug into the tissue and decoupling or removing the injection device from the tissue. In the context of the present disclosure, "Injection" should be distinguished from "infusion". An infusion device is permanently coupled to the tissue for an extended time period and virtually permanently, night and day, in some cases, for example in diabetes therapy by Continuous Subcutaneous Insulin Infusion.

For an injection of liquid insulin formulations, hand-held injection devices of the pen-type are commonly used. Those pen-type injection devices include, in an operable state, a typically cylindrical drug cartridge which holds a volume of typically between 1 ml and 3 ml of a liquid insulin formulation. The drug cartridge may be either replaceable by a device user or be readily built-in, resulting in the whole injection device being disposable. The injection device further includes an injection cannula for the subcutaneous injection or a coupler for such cannulas. Those pen-type injection devices further include a drive unit with a threaded spindle for controlled displacement of a plunger inside the drug cartridge, thus forcing defined drug volumes out of the cartridge and into the cannula. The drive unit further includes a dose setting control, typically in form of a dose setting knob with a scale, wherein manual rotation of the dose setting knob sets a desired drug volume to be injected.

The drive unit further includes a typically manually actuated injection actuator which is operated by the user for actually carrying out an injection. Typically, the injection actuator is integral with the dose setting knob, wherein the dose setting knob is pressed down, e.g. using a thumb, for carrying out the injection.

For most devices, the injection cannula, the drug cartridge and the drive unit, in particular the spindle, are arranged in-line, having a common longitudinal axis. This type of arrangement results in a pen-like shape, having a length of typically 10 cm to 20 cm and a typically circular or near-circular cross section of 1 cm to 3 cm in diameter. For carrying out an injection, the user first sets the dose to be injected, typically with one hand holding the device and the other hand operating the dose setting knob. For carrying out the injection, the device is held in a fist, the cannula is inserted into the tissue, e.g. of an arm or leg, followed by the thumb of the holding hand pressing down the dose setting knob.

In some devices, the drive unit includes an electrical drive unit, typically including a rotary motor with gearbox and corresponding control circuitry, rather than a manually operated drive. Those devices are somewhat more convenient and may offer additional functionality, such as automatic logging of injections, including download to a standard Personal Computer (PC or the like). The general way of operation, however, is identical.

SUMMARY

In at least one embodiment of the present disclosure, a hand-held injection device for the metered injection of a liquid drug into a person's tissue is disclosed. In an exemplary embodiment, the injection device comprises an elongated drug reservoir having a longitudinal reservoir axis (A), and an elongated dosing unit having a dosing unit inlet, a dosing unit outlet, and a metering cavity, the dosing unit having a longitudinal dosing unit axis (A'), the elongated drug reservoir being fluidically coupled to the dosing unit inlet. Wherein the dosing unit and the drug reservoir are arranged such that the longitudinal dosing unit axis (A') is in parallel alignment with the reservoir axis (A). Wherein the dosing unit is structured to allow the flow of the liquid drug from the drug reservoir into the metering cavity via the dosing unit inlet, thus charging the metering cavity, and to subsequently discharge the metering cavity by dosing drug out of the metering cavity into the dosing unit outlet. Wherein the elongated dosing unit includes a drive coupler for coupling the dosing unit of the elongated dosing unit to an actuator for the application time, such that operation of the actuator results in the metering cavity being charged or discharged, respectively.

In at least one embodiment of the present disclosure, the hand-held injection device is structured, subsequent to charging the metering cavity, to stepwise discharge the metering cavity in a number of separate injections. Further, in an embodiment of the hand-held device, the device may also comprise a user-operated dose setting control, the user-operated dose setting control being coupled to the dosing unit for setting an individual dose volume for each injection.

In at least one embodiment of the present disclosure, the dosing unit may include a valve arrangement, where the valve arrangement is switchable between an inlet state and an outlet state, such that, in the inlet state, the dosing unit inlet is fluidically coupled to the metering cavity and the dosing unit outlet is fluidically separated from the metering cavity, wherein in the outlet state, the metering cavity is fluidically coupled with the dosing unit outlet and the dosing unit inlet is fluidically separated from the metering cavity.

In at least one embodiment of the present disclosure, the elongated dosing unit includes a stationary member and a movable member, the movable member includes the dosing cavity, wherein the movable member and the stationary member, in combination, form the valve arrangement such that a relative motion of the movable member with respect to the stationary member switches the valve arrangement between the inlet state and the outlet state.

In at least one embodiment of the present disclosure, the elongated dosing unit includes a piston pump, the piston pump including a piston, the piston being linearly displaceable in the metering cavity between a proximal end position and a distal end position for charging and discharging the metering cavity. Further, the piston may also include an encoder scale.

In at least one embodiment of the present disclosure, the drive coupler is structured to couple to a single actuator for switching the valve arrangement between the inlet state and the outlet state and alternatively charging and discharging the metering cavity. The dosing unit may also include a piston pump that includes a piston. The piston being linearly displaceable in the metering cavity between a proximal end position and a distal end position for charging and discharging the metering cavity, wherein the dosing unit is designed to couple the piston for an application time of the dosing unit, continuously to the actuator and to selectively frictionally couple the movable member to the actuator for switching the valve arrangement between inlet state and outlet state.

The selective frictional coupling of the movable member to the actuator may also be independent from the coupling of the piston to the actuator in at least one embodiment.

In at least one embodiment of the present disclosure, the hand-held injection device may also comprise a drive unit having a single actuator. Additionally, the single actuator may be an electric motor and the hand-held injection device further includes control circuitry, the control circuitry being operatively coupled to the electric motor. Further, the drive unit may also have a longitudinal drive unit axis, the longitudinal drive unit axis being in-line with or parallel to the longitudinal dosing unit axis (A').

In at least one embodiment of the present disclosure, the hand-held injection device may also comprise a biasing device, the biasing device pressurizing the drug inside the drug reservoir.

In at least one embodiment of the present disclosure, the hand-held injection device may also comprise a cannula coupler or a port coupler, releasably mechanically coupling the hand-held injection device to an injection cannula or a subcutaneous port and structured to releasably fluidically couple the dosing unit outlet with the injection cannula or the subcutaneous port. Additionally, the cannula coupler or the port coupler may also be arranged to couple the hand-held injection device and the injection cannula or the subcutaneous port such that the longitudinal reservoir axis (A) is perpendicular to longitudinal cannula axis or port axis.

In at least one embodiment of the present disclosure, the hand-held injection device may also comprise a user-operable reservoir coupler.

In at least one embodiment of the present disclosure, the hand-held injection device may also comprise including a measurement device, the measurement device operable to determine a presence and/or a concentration of an analyte within a human's blood.

In at least one embodiment of the present disclosure, the hand-held injection device may also comprise a disposable module, the disposable module including the dosing unit, the hand-held injection device further including a reusable module, the reusable module including circuitry, wherein the disposable module and the reusable module are designed to releasably couple such that the disposable module is disposable by a device user with the reusable module being maintained for subsequently coupling with a further disposable module.

In at least one embodiment of the present disclosure, an injection device kit is disclosed. An exemplary embodiment of the injection device kit comprises a disposable module comprising an elongated drug reservoir and a dosing unit, the elongated dosing unit having a dosing unit inlet, a dosing unit outlet, and a metering cavity, the dosing unit having a longitudinal dosing unit axis (A'), the elongated drug reservoir being fluidically coupled to the dosing unit inlet, and a reusable module comprising circuitry and a drive unit; wherein the reusable module and the disposable module are structured to be coupled together by a user, In at least one embodiment of the present disclosure, a disposable module is disclosed. The disposable module, according to at least one embodiment, includes (a) a reservoir coupler for coupling to an elongated drug reservoir, the drug reservoir having a longitudinal reservoir axis (A) and a drug reservoir outlet, (b) an elongated dosing unit, the dosing unit having a dosing unit inlet, a dosing unit outlet, and a metering cavity, the dosing unit having a longitudinal dosing unit axis (A'), the reservoir coupler being fluidically coupled to the dosing unit inlet, where the dosing unit and the reservoir coupler are designed such that, when a drug reservoir is coupled to the reservoir coupler, the longitudinal dosing unit axis (A') is in parallel alignment with drug reservoir axis (A). Further, the dosing unit of the disposable module may be designed to charge the metering cavity by drawing drug from the drug reservoir into the metering cavity via the reservoir coupler and the dosing unit inlet, and to subsequently discharge the metering cavity by dosing drug out of the metering cavity into the dosing unit outlet. Additionally, the dosing unit of the disposable module may further include a drive coupler for coupling the dosing unit for the application time of the dosing unit to an actuator, such that operation of the actuator results in the metering cavity being charged or discharged, respectively. The disposable module may also include a drug reservoir.

In at least one embodiment of the present disclosure, the hand-held injection device includes an embodiment of the disposable module.

In at least one embodiment of the present disclosure, a method for the metered injection of a liquid drug into a person's tissue is described. The method, according to at least one embodiment, comprise providing a hand-held injection device, where the hand-held injection device includes an elongated drug reservoir, the drug reservoir having a longitudinal reservoir axis (A), an elongated dosing unit, the elongated dosing unit having a dosing unit inlet, a dosing unit outlet, and a metering cavity, the dosing unit having a longitudinal dosing unit axis (A'), the drug reservoir being fluidically coupled to the dosing unit inlet, the dosing unit and the drug reservoir being arranged such that the longitudinal dosing unit axis (A') is in parallel alignment with the reservoir axis (A). The exemplary method also includes charging the metering cavity by drawing drug from the drug reservoir into the metering cavity via the dosing unit inlet, and subsequently discharging the metering cavity by dosing drug out of the metering cavity into the dosing unit outlet.

BRIEF DESCRIPTION OF THE DRAWINGS

The features and advantages of the present disclosure, and the manner of attaining them, will be more apparent and better understood by reference to the following descriptions taken in conjunction with the accompanying figures, wherein.

DETAILED DESCRIPTION

Figure 1:
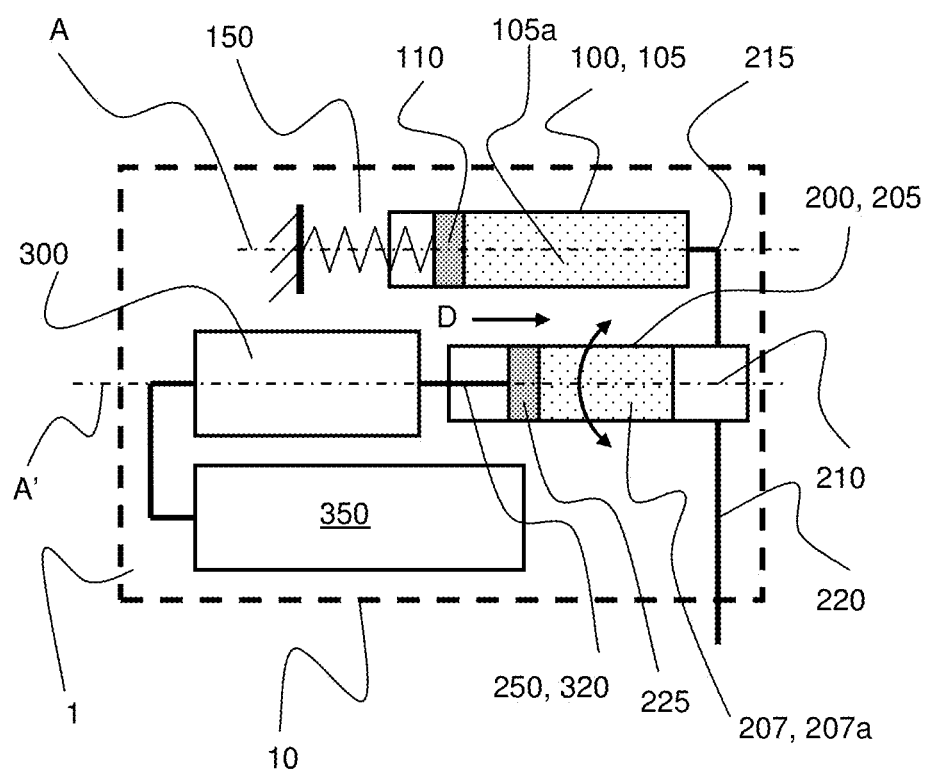
FIG. 1 shows an injection device in a schematic structural and functional view, according to at least one embodiment of the present disclosure.

While a pen-type insulin injection device is easier, safer and more discrete as compared to the usage of a standard syringe, the discreetness of pen-type devices is limited due to the considerable device length. Injection of insulin is typically required in the context of each meal intake, e.g. shortly before the meal, and therefore must often be carried out in public, e.g. in a cafe or restaurant. Maximum discreetness is therefore crucial for many Persons with Diabetes (PwDs).

Some hand-held injection devices do therefore not include a rigid threaded spindle, but a more flexible structure, such as an elongated threaded element of a flexible material or an arrangement of rigid thread elements that are coupled by flexible links, thus forming a chain-like structure. Those devices allow bending the threaded element in parallel to the drug cartridge, thus reducing the device length. The achievable length reduction, however, is limited. In addition, the design of the drive unit is complex.

In at least one embodiment of the present disclosure, a device is disclosed which provides improved hand-held injection devices for the metered administration of a liquid drug that allows a more discrete usage in typical everyday situations. In at least one embodiment, this more discrete usage is achieved based on the insight that the length of the injection device can be reduced—in comparison to a pen-type device—by providing a fluidic dosing unit downstream, that is, at the outlet, of a drug reservoir and in parallel arrangement with the drug reservoir.

In at least one embodiment of the present disclosure, a hand-held injection device for the metered injection of a liquid drug into a person's tissue is described. Such a device may include:
a) an elongated drug reservoir, the drug reservoir having a longitudinal reservoir axis,
b) an elongated dosing unit, the dosing unit having a dosing unit inlet, a dosing unit outlet, and a metering cavity, the dosing unit having a longitudinal dosing unit axis, the drug reservoir being fluidically coupled to the dosing unit inlet,
the dosing unit and the reservoir being arranged such that the longitudinal dosing unit axis is in parallel alignment with the reservoir axis,
the dosing unit being designed to charge the metering cavity by drawing drug from the drug reservoir into the metering cavity via the coupler and the dosing unit inlet, and to subsequently discharge the metering cavity by dosing drug out of the metering cavity into the dosing unit outlet.

The dosing unit may include a drive coupler for coupling the dosing unit for the application time of the dosing unit to an actuator, such that operation of the actuator results in the metering cavity being charged or discharged, respectively.

The term "elongated" in the context of the drug reservoir and the dosing unit indicates that both the drug reservoir and the dosing unit have a longitudinal dimension that is long as compared to the other dimensions. A longitudinal axis is an axis along the elongated dimension. The parallel alignment of dosing unit axis and reservoir axis is a side-by-side arrangement with the axis being spaced apart.

The application time is the total time for which the dosing unit is used before it is discarded. The application time is may be referred to in days.

The dosing unit inlet and the dosing unit outlet in at least one embodiment are distinct from each other.

The term "dosing" refers to a metered administration of a well-defined and typically selectable drug volume that is generally smaller than and small as compared to a maximum filling volume of the metering cavity during operation.

In some embodiments, the drug reservoir is a cartridge, the cartridge having a cartridge body extending along a longitudinal cartridge axis and a cartridge plunger, the cartridge plunger being sealing displaceable inside the cartridge body from a proximal to a more distal plunger position as drug is drawn out of the reservoir outlet.

The cartridge body is typically made from glass but may also be made from other materials, such as medical-grade plastics. The cartridge may be a standard cartridge, e.g. an insulin cartridge, as widely available for use in pen-type injection devices.

In some embodiments, the injection device includes a biasing device, the biasing device pressurizing the drug inside the drug reservoir.

As will be discussed below, the dosing unit may actively create some amount of suction pressure for drawing drug out of the reservoir. It may also or instead generate some over pressure inside the drug reservoir. In case of a cartridge having a cartridge, plunger, for example, the plunger friction may be too high to be reliably overcome by the fluidic suction pressure. Therefore, a biasing element, realized e.g. as a spring, may be used to provide a continuous biasing force in the delivery direction. Because the dosing, however, is controlled by the dosing unit downstream of the reservoir, the biasing force is not critical and does not need to be constant over the displacement distance of the cartridge plunger.

Alternatively to a cartridge as discussed above, the drug reservoir may be an elongated flexible pouch or bag and be made, e.g., from foil sheets. In a further alternative, the drug reservoir is semi-flexible, including a rigid body or base that is, e.g., made from plastic, and a flexible cover sheet. The drug reservoir may be filled by the user prior to application or may be provided readily filled. For flexible or semi-flexible reservoirs, a biasing device is typically not required, but may be present as well. A flexible or semi-flexible reservoir typically allows greater design flexibility with respect to minimizing the required overall size. In addition, frictional losses that are typical for a cartridge due to the plunger friction are considerably reduced and may even be negligible.

In some embodiments, the drug reservoir has a capacity in a range of about 1 ml to about 5 ml. Filling volumes that may be used in some embodiments are any ranges up to full capacity, e.g., 1.5 ml and 3 ml. The drug reservoir may be provided empty and be filled, typically by a device user, prior to application, or may be provided readily filled.

In some embodiments, the device includes a user-operated dose setting control, the dose setting control being coupled to the dosing unit for setting an individual dose volume for each injection.

The dose setting control may be a dedicated control element, such as a dose setting knob, or may be integral part of a general-purpose user interface of the device. An injection actuator may be provided separate from or integral with the dose setting control. For applications where only a fixed dose volume needs to be injected, the dose setting control may be omitted.

In some embodiments, the injection device is designed, subsequent to charging the metering cavity, to stepwise discharge the metering cavity in a number of separate injections. In such an embodiment, each injection is separately triggered by a device user. Stepwise discharging the metering cavity may be realized by providing a displacement member, such as a piston inside a generally stiff metering cavity and stepwise displacing the displacement member from a most proximal to a most distal piston position inside the metering cavity as will be discussed below in more detail. Alternatively, the metering cavity may have elastic walls and a displacement member, such as a pushing plate may be arranged outside the metering cavity.

In some embodiments, the dosing unit includes a valve arrangement, the valve arrangement being switchable between an inlet state and an outlet state, such that, in the inlet state, the dosing unit inlet fluidically couples with the metering cavity while the dosing unit outlet is fluidically separated from the metering cavity and that, in the outlet state, metering couples with the dosing unit outlet with the dosing unit inlet being fluidically separated from the metering cavity.

A capacity or maximum charging volume of the metering cavity is considerably smaller than a maximum filling volume or capacity of drug reservoir with a typical ratio being in a range of 1:5 to 1:100, e.g. 1:30. If the hand-held injection device includes or is used in combination with a standard drug cartridge holding 300 IU of liquid insulin formulation of concentration U100, for example, the maximum charging volume of the metering cavity may, e.g., be 10 IU.

During the application time of a single drug reservoir, the metering cavity therefore needs to be repeatedly recharged. Therefore, switching between the inlet state and the outlet state is repeatedly carried out. The valve arrangement is switched to the inlet state for charging the metering cavity and subsequently switched to the outlet state for discharging the metering cavity in a number of separate injections.

While various approaches and strategies may be used for determining particularly suited times or remaining drug volumes of the metering cavity for recharging the metering cavity, as well as for determining a level to which the metering cavity is charged or recharged, it is often favorable to recharge the metering cavity if is empty or close to being empty and to generally charge the metering cavity to its maximum charging volume. For these embodiments, the valve arrangement is therefore in the outlet state most of the time and only temporary switched to the inlet state for recharging. Alternatively, however, the metering cavity may be charged individually for each injection and be discharged or empty in between.

In some embodiments including a valve arrangement, the dosing unit includes a stationary member and a movable member, the movable member including the metering cavity, the movable member and the stationary member, in combination, forming the valve arrangement such that a relative motion of the movable member with respect to the stationary member switches the valve arrangement between the inlet state and the outlet state.

The dosing unit inlet and the dosing unit outlet are included in the stationary member, typically in the form of corresponding fluidic apertures. Flow channels or forming a dosing unit inlet conduit and the dosing unit outlet conduit may be included in the stationary member and be fluidically coupled to the dosing unit inlet and the dosing unit outlet, respectively. The dosing unit inlet conduit and/or the dosing unit outlet conduit may be integral with the dosing unit inlet and the dosing unit outlet, respectively. The conduits and the stationary member may be formed in a single component, for example by injection molded plastics.

The movable member includes a metering cavity aperture that couples, in dependence of a position of the movable member with respect to the stationary member, the metering cavity fluidically with the dosing unit inlet or the dosing unit outlet. Besides the inlet state and the outlet state, a further isolated state may be provided in which the metering cavity is neither fluidically coupled with the dosing unit inlet nor the dosing unit outlet. The design may especially be such that when switching between the inlet state and the outlet state, the isolated state is passed as an intermediate state. A simultaneous coupling of the metering cavity aperture with the dosing unit inlet and the dosing unit outlet is generally excluded.

For establishing a non-leaking fluidic connection of the metering cavity aperture with the dosing unit inlet or the dosing unit outlet, respectively, and for closing the non-connected of the dosing unit inlet and the dosing unit outlet, elastic sealing elements, such as rubber elements, or a soft plastic component, may be provided. A soft plastic component may be realized together with either or both of the movable member or the stationary member in a two-component injection molding process. Alternatively, hard-hard sealing may be used. Both the stationary member and the movable member are typically made from plastic, but may also be made from other materials such as metal or ceramic.

In some embodiments, the motion of the movable member for switching between inlet state and outlet state is a pure rotational movement about the longitudinal dosing unit axis with the stationary member serving as rotational bearing for the movable member. Alternatively, however, the movement may be linear.

In some embodiments, the injection device includes a piston pump, the piston pump including a piston, the piston being linearly displaceable in the metering cavity between a proximal end position and a distal end position for charging and discharging the metering cavity. In such embodiments, the piston serves as displacement member. The displacement range of the piston may be mechanically restricted to the distance between proximal end position and distal end position. The drug-filled active volume of the metering cavity is maximum for the proximal end position and minimal and favorably virtually zero for the distal end position.

In some of those embodiments, the piston is designed to couple, for the application time of the dosing unit, to a drive unit.

For carrying out the dosing, the piston is favorably displaceable in a number of small and potentially virtually infinite small increments between the proximal and position and the distal end position. That is, the design is such that the metering cavity can be emptied in a number of small steps rather than fully emptying the filled metering cavity in a single stroke. Since for a piston pump, the volume that is displaced out of the metering cavity is proportional to the displacement distance of the piston, the smallest incremental displacement is a limiting factor for both the smallest volume that can be injected as well as for the achievable dose setting resolution for larger injections.

In combination with providing a metering cavity with a maximum filling volume that is considerably smaller than a maximum filling volume of the drug reservoir, this type of embodiment is favorable with respect to the dosing precision, since actual dosing is carried out from a volume that is smaller than the total drug volume in the cartridge. As compared to a standard pen-type injection device where dosing is generally carried out directly of the drug reservoir, the ratio of the smallest drug volume that can be injected to the total drug volume of the drug reservoir is smaller, thus improving the dosing precision for given manufacturing and component tolerances and precision.

Similarly, for the required dosing precision being constant, a dosing unit in accordance with the present disclosure allows the injection of liquid drugs having a higher effective concentration, thus reducing the size of the drug reservoir and the amount of liquid that is subcutaneously administered in a single injection. For example, rather than the currently typical insulin concentration U100 (corresponding to 100 International Units per ml of liquid formulation), insulin formulations with higher concentrations, such as U200 or even U500 may be used with acceptable dosing precision.

In at least one embodiment, the maximum filling volume of the metering cavity is sufficiently large to allow manufacture of the dosing unit by proven and cost-effective mass production processes, such as injection molding. In an exemplary design, the metering cavity is cylindrical with a piston displacement range between proximal end position and distal end position of about 5 mm and an inner diameter of about 9 mm.

For some embodiments having a piston pump, the metering cavity may be the cylindrical inner volume of a hollow cylinder, with the cylinder axis as center axis of the metering cavity defining the longitudinal dosing unit axis.

In embodiments where switching between the inlet state and the outlet state is carried out by rotating the movable member with respect to the stationary member, the axis of rotation for rotating the movable member and the center axis of the metering cavity favorably coincide. For those embodiments, switching is accordingly carried out by rotating the movable member about the center axis of the metering cavity.

A proximal face surface of the hollow cylinder is open to receive the piston. A distal face surface of the hollow cylinder is closed, with the metering cavity aperture being in the distal face surface or in the shell surface in proximity to the distal face surface. For each piston position, the liquid filled active volume of the metering cavity is given by the volume enclosed by the shell surface, the distal face surface and the piston. The active volume of the metering cavity is accordingly maximum for a the proximal end position of the piston and minimal and favorably virtually zero for the distal piston end position. For filling the metering cavity, the piston is accordingly moved in proximal direction thus generating—by increasing the active volume—a vacuum inside the metering cavity and drawing drug into the metering cavity. For dosing, the piston is moved in distal direction in the delivery direction, thus displacing—by reducing the active volume—drug out of the metering cavity. Between those operations, the valve state may be switched as explained above.

In some embodiments including a piston pump, the piston includes an encoder scale. The encoder scale may, e.g., be formed by a pattern of light and dark longitudinal stripes on the outer surface of a piston shaft. In combination with a corresponding sensor element, such as an optical refection sensor, the encoder scale forms a linear encoder for supervising and/or controlling the displacement motion of the piston.

In some embodiments including a piston pump, the dosing unit is designed to couple to a single actuator for switching the valve state between the inlet state and the outlet state and alternatively charging and discharging the metering cavity. As will be discussed below in the context of exemplary embodiments, alternatively switching the valve state and charging or discharging the metering cavity via a single actuator may be favorably realized via selective frictional coupling.

Switching the dosing unit between a first operational state where operation of a single actuator switches the valve state and a further operational state where operation of the actuator charges or discharges the metering cavity is favorably achieved by controlling a direction of operation of the actuator, in particular a rotational direction of a motor, alone or in combination with a linear piston position and or a rotational position of the movable member with respect to the stationary member. For such embodiments, only a single actuator is required for operating the dosing unit.

In some embodiments including a piston pump, the dosing unit is designed to couple the piston for an application time of the dosing unit, continuously to the actuator and to selectively frictionally couple the movable member to the actuator for switching the valve arrangement between inlet state and outlet state.

In some of those embodiments, the selective coupling of the movable member to the actuator is independent from the coupling of the piston to the actuator. The term "separate" indicates that a driving force and/or driving torque for switching the valve arrangement is transmitted from the actuator to the movable member independent from the piston coupling to the movable member and the piston does not serve as transmitter element. Alternatively, however, a driving force or driving torque for switching the valve arrangement may be transmitted via the piston as transmitter element, that is, the movable member selectively couples to the actuator via the piston.

In some embodiment of the dosing unit including a piston pump, the piston and the movable member are in threaded engagement. In a typical embodiment where the maximum charging capacity of the metering cavity is 10 IU of U100 insulin formulation, the spindle and the threaded engagement may be designed that the full piston displacement range between proximal end position and distal end position, respectively, corresponds to five full spindle rotations.

For realizing the piston displacement, the piston may include an elongated piston shaft that extends from a sealing distal end section in proximal direction, the piston shaft being designed for coupling to a drive unit. The piston or piston shaft may include a thread and a counter thread may be provided on the movable member, resulting in the displacement motion of the plunger inside the metering cavity being screw-like. Alternatively, a piston shaft may be a separate element proximal of the piston and coupling to the piston in a favorably play-free way. In some embodiments, the piston thread is an outside thread and the counter-thread is an inside thread which is, however, not essential. Favorably, the threaded engagement is substantially play free which may be achieved by axial and/or radial biasing of the thread.

In some of the above-discussed embodiments, the piston and the movable member are switchable between a coupled state and a decoupled state, such that, by operating the drive unit in the decoupled state, the piston is linearly displaceable within the metering cavity with a state of the valve arrangement being maintained, and that, by operating the drive unit in the coupled state, the state of valve arrangement is switchable between the inlet state and the outlet state with a position of the piston within the metering cavity being maintained.

This type of embodiment has the particular advantage that the operations of switching the valve state and displacing the piston are operationally separated by maintaining the piston position, and, accordingly, the liquid-filled active volume of the metering cavity, unchanged when switching the valve state, and vice versa. In this way, switching the valve state involves no significant dosing error. Favorably, the movable member and the piston move synchronously, that is, without relative motion, for switching the valve state. Alternatively, the movable member may rotate about the piston for switching the valve state without axial displacement.

In some embodiments, the injection device includes a drive unit, the drive unit including a single actuator.

In some embodiments, the single actuator is an electric motor and the injection device further includes control circuitry, the control circuitry being operatively coupled to the motor.

The control circuitry is typically micro-controller and/or ASIC based and in particular controls and favorably supervises operation of the electric motor. The control circuitry may further include additional units or be realized integral with further units and implement further functionality, such as a user interface or the input/output of events, information of data, memory for logging injections and further relevant invents, data interfaces for communication with further devices, such as a PC, an external blood glucose meter, etc.

In some embodiments including a drive unit, the drive unit has a longitudinal drive unit axis, the longitudinal drive unit axis being in-line with or parallel to the longitudinal dosing unit axis. This kind of arrangement allows a particular compact design that is well suited to be hand-held conveniently and discretely.

In some embodiments, the hand-held injection device includes a cannula coupler or a port coupler for releasably mechanically coupling the injection device to an injection cannula or a subcutaneous port and for releasably fluidically coupling the dosing unit outlet with the injection cannula or the subcutaneous port.

The phrase "releasably coupling" refers to a coupling that can be established and released by a device user during application without causing damage to the injection device, e.g. via a bayonet, a threaded engagement, a releasable snap-fit, or the like. An injection cannula may, for sterility and sharpness reasons, be designed and intended for a single injection, or may be designed for a number of consecutive injections.

Alternatively or additionally, the injection device may be designed to releasably couple mechanically and fluidically to a subcutaneous port via a port coupler. The subcutaneous port is inserted into the tissue and favorably adhesively attached to the skin prior to carrying out injections via the port. The subcutaneous port may include a subcutaneous port cannula in form of a rigid cannula, e.g. made from medical-grade stainless steel or suited plastics, or a soft cannula, e.g. made from Teflon. A subcutaneous port allows to reduce the number of generally disliked skin piercings to a smaller number, of e.g., once every few days when replacing the subcutaneous port. For carrying out injections, the drug is injected into a corresponding receiving cavity of the port rather than directly into the tissue, the receiving cavity being fluidically coupled with the subcutaneous cannula.

A port coupler may be provided on the injection device and a corresponding injection device coupler as counterpart may be provided on the subcutaneous port. The port coupler and the injection device coupler may be designed to ensure correct alignment of port and injection device in a loose fit without fixation, thus allowing easy removal of the injection device after an injection. Alternatively, a releasable fit, such as a soft snap-fit, may be provided.

The receiving cavity of the subcutaneous port may be covered and sealed by a pierceable sealing port septum.

In some embodiments including a cannula coupler or a port coupler, the cannula coupler or the port coupler is arranged to couple the injection device and the injection cannula or the subcutaneous port such that the longitudinal reservoir axis is perpendicular to a longitudinal cannula axis or port axis.

The injection device in at least one embodiment has a bottom surface that is parallel to the longitudinal reservoir axis. Because the cannula axis defines the direction of an insertion motion for the injection device for inserting the cannula perpendicularly into the tissue, this design allows an insertion with the bottom surface of the injection device being parallel with the skin. For injections into typical injection sites for self-injection, such as a forearm or thigh, this design allows carrying out the injection with a relaxed and convenient hand posture. In addition, for a typical and favorable size of the injection device, substantially the whole injection device may be covered by the hand while holding the device, thus allowing the injections to be particularly discrete. For a manually operated state-of-the-art pen-type injector, in contrast, an arrangement of the cannula axis perpendicular to the longitudinal reservoir axis is hardly possible since the dose setting knob, which has to be pressed down for carrying out the injection by the thumb of the hand holding the device, and the injection cannula are arranged at opposite end surfaces of the pen-shaped device housing. For an orientation of the cannula axis other than in-line with the longitudinal device axis, the required hand motion for inserting the cannula into the tissue would be complex. In addition, the insertion direction may be misaligned as compared to the cannula axis, causing considerable pain.

Alternatively or additionally, the injection device may be designed to couple to a cannula or port with the cannula axis or port axis being parallel to or in line with the longitudinal reservoir axis.

In some embodiments, the injection device further includes a user-operable reservoir coupler. For those embodiments, the drug reservoir may include a pierce-able sealing septum and the dosing unit inlet conduit may include a corresponding piercing cannula.

Providing the drug reservoir separate from the dosing unit has the advantage that the reservoir may be stored under especially suited conditions, for example in a refrigerator in the case of insulin, independent from the dosing unit. In some cases, standardized or quasi-standardized reservoirs may be used, such as insulin cylinder cartridges for pen-type injectors.

Providing the drug reservoir separate from the dosing unit therefore allows the user or a Health Care Professional (HCP) to select the best-suited insulin according to the individual needs, without a need for providing different types of dosing units. Furthermore, this type of embodiment allows using the same type of dosing unit with different types of drug reservoir, such as cylinder cartridges and pouch-like flexible reservoirs. In this context, an arrangement of the dosing unit downstream, that is, at the outlet of the reservoir is of particular advantage since it functionally decouples the dosing and the dosing precision largely from the reservoir properties.

In alternative designs, however, the drug reservoir and the dosing unit are provided as a readily assembled unit, thus allowing the handling to be especially simple and the number of handling steps to be carried out by the user to be particularly small.

The reservoir coupler may include a holding structure, such as an elastic collar and/or a tubular element, for mechanically supporting and aligning the drug reservoir, and may further include a fluidic reservoir coupler, such as a piercing cannula for piercing a septum of the drug reservoir.

In some embodiments, the injection device includes a measurement device, the measurement device being designed to determine a presence and/or a concentration of an analyte within a human's blood.

The analyte may be an analyte the presence and/or concentration of which is of interest in the context of the specific therapy, and in particular for drug injection to be administered. In the context of diabetes the analyte may especially be blood glucose, but may also be, additionally or alternatively, a further analyte such as blood ketone.

In the exemplary case of the analyte being blood glucose, the measurement device is typically based on an electro-chemical or electro-optical principle and are used with single-used test strips. Such measurement devices are commercially available, e.g., under the brand ACCU-CHEK® Aviva, ACCU-CHEK® Performa, ACCU-CHEK® Mobile by Roche Diagnostics.

Measurement results may be directly displayed to a device user by a display included in the injection device, such as a graphical or alphanumerical LCD or (O)LED display. Additionally or alternatively, measurement results are, together with a time stamp, stored in a record memory for later recall.

The injection device may further include a bolus calculator to calculate and display recommended drug doses, such as insulin doses, do be injected, based factors such as a blood analyte measurement result, intended meal intakes, previous injections, general health condition, sportive activities, and the like. Corresponding algorithms are generally based on a proportional relationship between carbohydrate intake and required insulin dose. Further algorithms are disclosed, e.g. in the WO 2006/021430.

In embodiments including an actuator such as a motor as discussed above, the bolus calculator may be coupled to the control circuitry of the actuator to directly control the actuator for the injection of a previously calculated drug dose. Alternatively, a recommended injection dose may be read by a device user and subsequently programmed for injection manually. In embodiments including a manually operated drive unit, the dose to be injected is set manually. Favorably, injected doses are stored, together with a time stamp, in a record memory.

A measurement device may be realized, fully or partly, integral with the control circuitry of a drive unit and/or further device circuitry.

In some embodiments, the injection device includes a disposable module, the disposable module including the dosing unit. Such an injection device may further include a reusable module, the reusable module including circuitry. The disposable module and the reusable module may be designed to releasably couple such that the disposable module is disposable by a device user with the reusable module being maintained for subsequently coupling with a further disposable module.

For this type of modular design, those components that may be designed for an extended lifetime in the range of typically several months up to several years, may be used for a comparatively long time, while the drug reservoir and drug-contacting elements, in particular the dosing unit, are replaced after a short lifetime of typically some days.

The circuitry may include functionality of the drive unit control, a measurement device, a bolus calculator, and record keeping functionality as discussed above. The circuitry may further include either or multiple of power supply circuitry, alarm clock, communication interfaces for typically wireless communication with further devices, such as a PC, and the like. The circuitry may be realized by general-purpose components, and/or application specific components, including ASICS and/or micro-controllers running corresponding firmware code.

The injection device may further include a drive unit which may be integral with the circuitry or the dosing unit, depending on the costs and design of the drive unit. A drive unit including an electric actuator would typically be designed for an extended application time and accordingly be realized integral with the circuitry, while a manually operated drive unit may be realized integral with the dosing unit.

According to a further aspect, the present disclosure is directed towards an injection device kit. The injection device kit may include a reusable module and a number of disposable modules, wherein the reusable module and either of the number of disposable modules are designed to be coupled by a device user, thus forming a modular injection device as discussed above.

A kit may, e.g., include one reusable module and a number of e.g., five, 10, or 20 separate disposable modules. In case that the injection device includes a drive unit with an electrically powered actuator, the drive unit may be integral with the circuitry. In such a kit, the disposable modules may be provided with readily filled drug reservoirs attached to or separate from the dosing units, with empty drug reservoirs to be filled by the device user attached to or separate from the dosing units, or without drug reservoir.

According to a still further aspect, the present disclosure is directed towards a disposable module. The disposable module may include
a) a reservoir coupler for coupling to an elongated drug reservoir, the drug reservoir having a longitudinal axis and a drug reservoir outlet,
b) an elongated dosing unit, the dosing unit having a dosing unit inlet, a dosing unit outlet, and a metering cavity, the dosing unit having a longitudinal dosing unit axis, the reservoir coupler being fluidically coupled to the dosing unit inlet, the dosing unit and the reservoir coupler being designed such that, when a drug reservoir is coupled to the reservoir coupler, the longitudinal dosing unit axis is in parallel alignment with drug reservoir axis, the dosing unit being designed to charge the metering cavity by drawing drug from the drug reservoir into the metering cavity via the reservoir coupler and the dosing unit inlet, and to subsequently discharge the metering cavity by dosing drug out of the metering cavity into the dosing unit outlet.

The dosing unit of the disposable module further includes a drive coupler for coupling the dosing unit for the application time of the dosing unit to an actuator, such that operation of the actuator results in the metering cavity being charged or discharged, respectively.

According to a still further aspect, the present disclosure is directed towards a hand-held injection device (1), including a disposable module discussed above.

According to at least one aspect, the present disclosure is directed towards the uses of a disposable module as discussed above as part of a hand-held injection device or an injection device kit as discussed above.

According to at least one aspect, the present disclosure is directed towards a method for the metered injection of a liquid drug into a person's tissue, the method including:
a) providing a hand-held injection device (1), the hand-held injection device (1) including
  an elongated drug reservoir (100), the drug reservoir (100) having a longitudinal reservoir axis (A),
  an elongated dosing unit (200), the dosing unit (200) having a dosing unit inlet, a dosing unit outlet, and a metering cavity (207), the dosing unit (200) having a longitudinal dosing unit axis (A'), the drug reservoir (100) being fluidically coupled to the dosing unit inlet (215a),
  the dosing unit (200) and the drug reservoir (100) being arranged such that the longitudinal dosing unit axis (A') is in parallel alignment with the reservoir axis (A),
b) charging the metering cavity (207) by drawing drug from the drug reservoir (100) into the metering cavity (207) via the dosing unit inlet (215a), and
c) subsequently discharging the metering cavity by dosing drug out of the metering cavity (207) into the dosing unit outlet (220a).

According to at least one aspect, the present disclosure is directed towards a method of providing a hand-held injection device for the metered injection of a liquid drug into a person's tissue, the method including
  a) providing a disposable module as discussed above,
  b) providing a drug reservoir
  c) coupling the drug reservoir to the reservoir coupler,
  d) providing a reusable module, the reusable module including circuitry and an actuator,
  e) releasably coupling, for the application time of the disposable module the disposable unit and the reusable module such that the actuator (305) couples to the drive coupler.

The disclosed methods may especially be carried out with devices, modules and kits as disclosed and further below. Therefore, embodiments and examples provided in the context of those devices, methods and kits may be used to detail embodiments of the disclosed methods, and vice versa.

FIG. 1 shows an embodiment of hand-held injection device 1 the components which are enclosed by a housing 10, housing 10 being a single part housing or alternatively a modular multi-part housing. Housing 10 may be split into a reusable housing and a disposable housing, the reusable housing enclosing a reusable module and the disposable housing enclosing a disposable module of the hand-held injection device.

A embodiment of Injection device 1 includes a drug reservoir 100, which is exemplary shown as cylindrical glass cartridge with a cartridge body 105 with a drug-filled cartridge portion 105a, and a plunger 110 that is displaceable inside cartridge body 105 along a longitudinal reservoir axis A. An exemplary glass cartridge that is typically used in pen-type insulin injection devices may, e.g., have a length in a range of 4 cm to 6 cm and an inner diameter of about 9 mm. Alternatively to a cartridge, the drug reservoir 100 may be an elongated flexible or semi-flexible bag or pouch.

An optional biasing device 150 in form of a spring is provided to exert a biasing force onto the plunger 110.

Dosing unit inlet conduit 215 fluidically couples drug reservoir 100 with dosing unit 200. Dosing unit 200 includes a movable member 205 in form of a hollow cylinder, the hollow cylinder having a closed distal end surface and an open proximal end surface. Dosing unit 200 further includes a stationary member 210. Movable member 205 and stationary member 210, in combination, form a valve arrangement. Stationary member 210 further serves as rotatory bearing for the movable member 205. Dosing unit 200 has a longitudinal dosing unit axis A' that is parallel with longitudinal reservoir axis A.

Dosing unit outlet conduit 220 fluidically couples dosing unit 200 with an injection cannula (not shown). Stationary member 210, dosing unit inlet conduit 215 and dosing unit outlet 220 are favorably realized integral by an injection-molded component which may also include a reservoir coupler for drug reservoir 100. The cylindrical inner volume of movable member 205 forms metering cavity 207. Piston 225 is sealing arranged inside the metering cavity 207 and is displaceable along longitudinal dosing unit axis A' in and against delivery direction D. Piston 225 and a closed distal front surface (not referenced), in combination, define a drug-filled active volume 207a of metering cavity 207. Dosing unit axis A' is a common symmetry axis of metering cavity 207 and piston 225.

By rotating movable member 205 with respect to stationary member 210, the valve state is switchable between an inlet state for drawing drug from the drug-filled cartridge section 105a into the metering cavity 207, thus charging the metering cavity 207 by increasing the active volume 207a, and an outlet state for discharging the metering cavity 207 by reducing the active volume 207a.

Figure 2A:
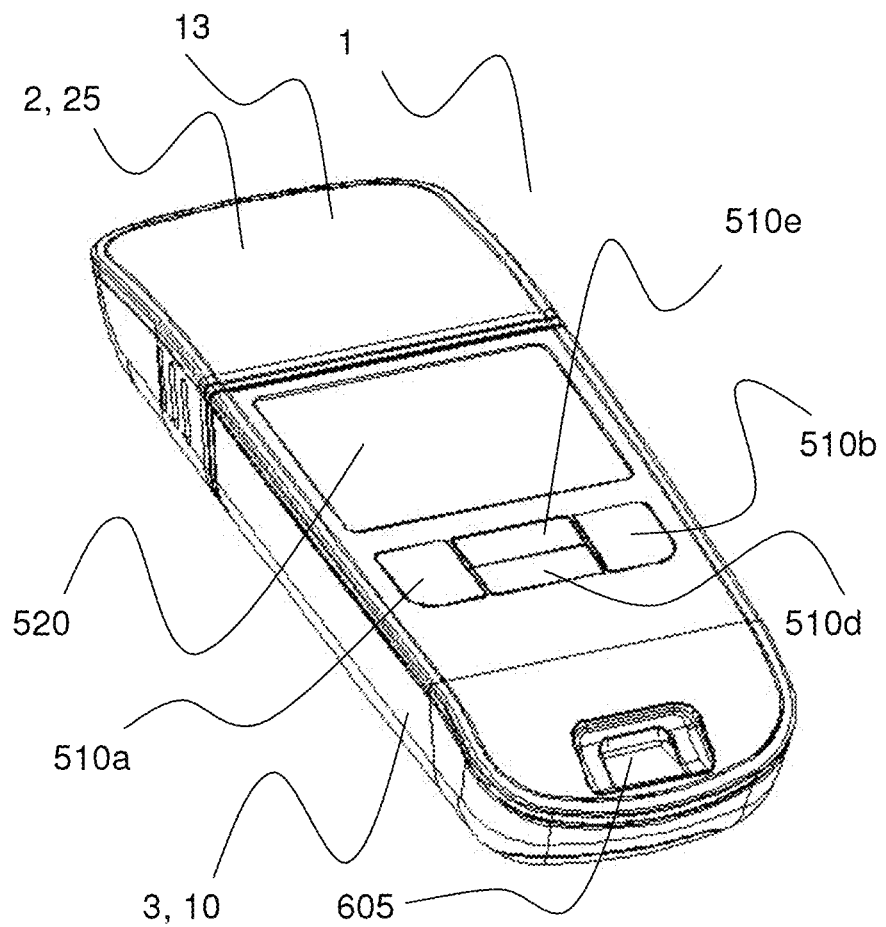
FIGS. 2A, 2B, and 2C each show an injection device in a schematic perspective view, according to at least one embodiment of the present disclosure.
Figure 2B:
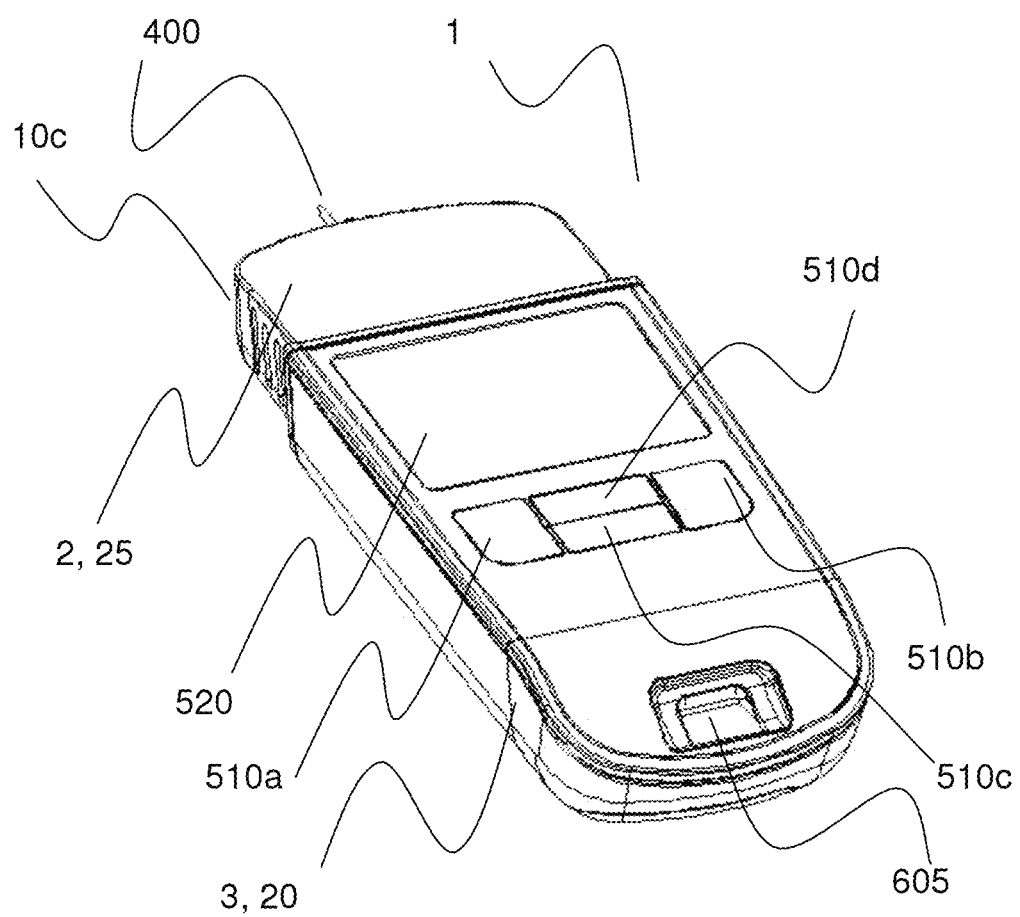
Figure 2C:
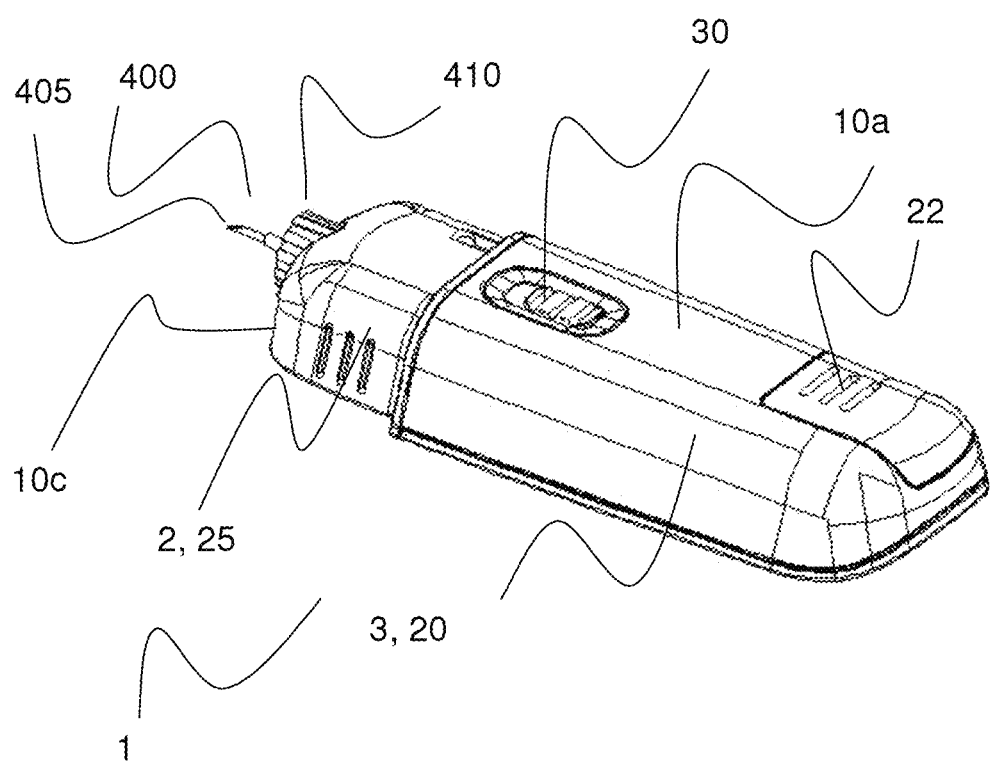
Figure 3:
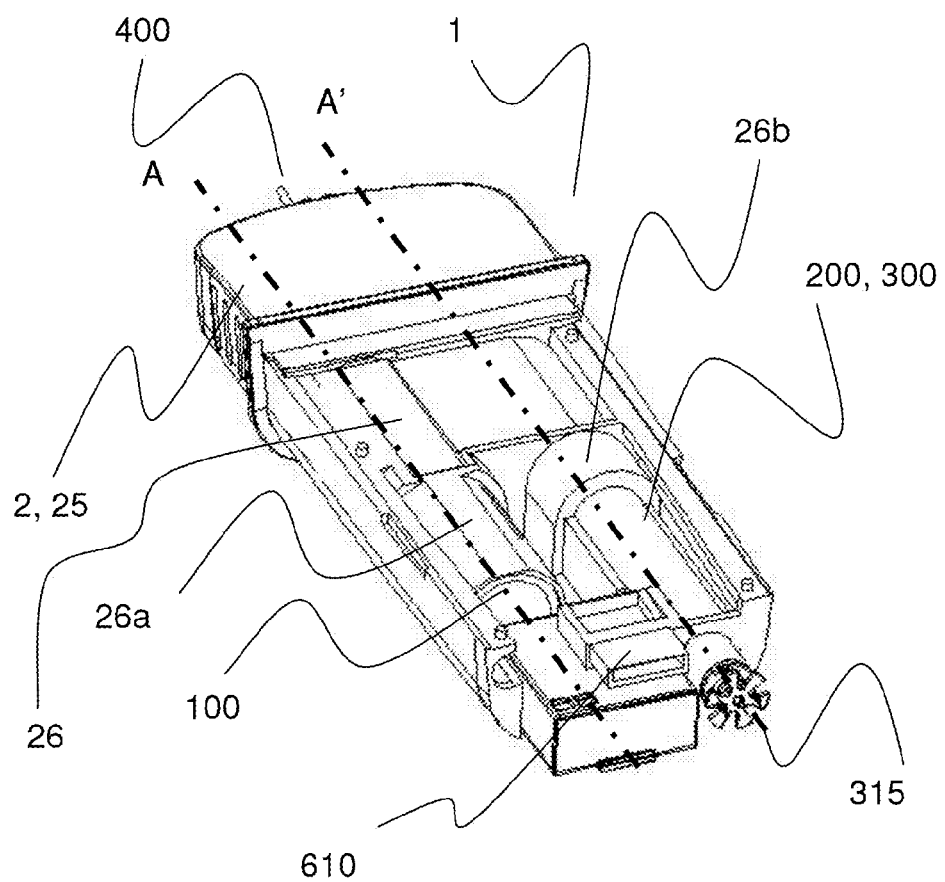
FIG. 3 shows an injection device in a schematic perspective view, according to at least one embodiment of the present disclosure.

Dosing unit 200 may in particular any of those dosing units as disclosed on FIG. 1 to FIG. 3. of application EP 2163273A1. Reference is made therefore to the disclosure of these figures and corresponding description for further details on the dosing unit. Dosing unit 200 may further be designed according to any embodiment as discussed above and further below in this document. Here and in the following, only those aspects of the dosing unit are discussed which may deviate from the disclosure of EP 2163273A1 or where specific aspects have to be considered.

A reversible drive unit 300 with an electric actuator, and circuitry 350 are further provided. Circuitry 350 in particular includes control circuitry for controlling drive 300. Drive unit 300 and piston 225 are coupled via a releasable drive coupler, the drive coupler including a disposable drive coupler 250, 320 as will be discussed below. Drive 300 may include a motor, such as a standard DC motor, a brushless or electronically commutated DC motor (EC motor) or a stepper motor and an optional reduction gear (not shown). Feedback to control circuitry 350 may be provided by an encoder of drive unit 300 and/or a further encoder including an encoder scale on piston 325, as will be discussed below.

In FIG. 1, drive unit 300 and dosing unit 200 are shown inline and in axial alignment, with the longitudinal drive unit axis A' being also a longitudinal axis of drive unit 300. Alternatively, however, a longitudinal axis of drive unit 300 (as defined, e.g., by a motor axis) may be shifted with relative to longitudinal dosing unit axis A'. For example, drive 300 may be arranged side-by-side and in parallel arrangement with dosing unit 200.

It should be noted that FIG. 1 does not imply any specific geometric arrangement of circuitry 350. In fact, the components and functional units of circuitry 350, including control circuitry for drive 300 as well as further circuitry and components such as user interface, displays, audio and/or vibratory indicators, and power supply, e.g. a rechargeable or non-rechargeable battery, may be arranged according to general design constraints and may also be distributed in order to best fill the available space and to achieve a compact design. It should further be noted that the filling volume of cartridge 100 and the volume of metering cavity 207 are shown to be in a similar range for clarity. In typical embodiments, however, the inner volume and accordingly a maximum liquid-filled active volume of metering cavity 207 would be considerably smaller as compared to the reservoir filling volume.

FIG. 2a shows an exemplary device 1 in a schematic perspective view. The housing of device 1 is sized and shaped to be comfortably grasped by a user with a single hand in a way that allows operation of pushbuttons 510, 510b, 510c, 510d.

Push buttons 505a, 505 b, 510a, 510b, 510c, 510d are part of a user interface of injection device 1. The user interface further includes a display 520 as well as favorably either of both of an acoustic indicator, such as a buzzer or loudspeaker, and a tactile indicator, such as a pager vibrator. It should be noted that the user interface as described and shown is exemplarily described for illustrative purposes. For example, the pushbuttons may be arranged differently and/or more or less pushbuttons may be used. Alternative control elements, such as a scroll wheel or a touch screen may be provided. Optical indicators such as LEDs may be provided additionally or alternatively to display 520, etc.

Pushbuttons 510a, 510b, 510c, 510d serve, together with display 520, as dose setting control, as injection trigger control, and for general operation and control of device 1, such as for controlling a blood glucose meter included in device 1, setting a device-internal clock, entering food data, reviewing a device-internal logbook memory of past injections, uploading logbook date from device 1 to an external device, such as a PC, etc.

FIG. 2a further shows a test strip port 605, the test strip port 605 being part of an optional blood glucose measurement device and being designed to receive an optical or electro-chemical single-use test strip. Alternatively, injection device 1 may include a blood glucose meter including a cassette, the cassette carrying a larger number of optical or electro-chemical test fields and allow doing a number of blood glucose measurements in sequence without having to replace a disposable. The blood glucose measurement device is controlled via the user interface of injection device 1 as described above and forms an integral part of device 1.

In the embodiment of FIG. 2, housing 10 as shown in FIG. 1 is split into disposable housing 25 and reusable housing 20, disposable housing 25 forming the housing of a disposable module 2 and reusable housing 20 forming the housing of a reusable module 3.

FIG. 2a further shows removable cap 13 that covers and protects a cannula coupler of device 1 and is coupled to disposable housing 25 e.g. via a snap-fit. Cap 13 is typically in place while transporting and storing injection device 1 and is only temporary removed for the injections. Favorably, cap 13 is shaped such that it allows an injection cannula to be attached with cap 13 being in place. Cap 13 may be a disposable product and an individual cap 13 may be provided with each disposable module 3. FIG. 2b shows the same view as FIG. 1 with cap 13 being removed. A releasably coupable injection cannula 400 is shown attached to injection device 1, injection cannula 400 projecting perpendicularly from a housing front surface 10c.

Reusable module 3 includes a power supply as well as drive unit 300 and circuitry 350, including user interface. Disposable module 2 carries all disposable components that are intended be used for emptying a single drug reservoir 100 and to be discarded afterwards. Disposable module 2 in particular includes dosing unit 200 and drug reservoir 100 and/or a reservoir coupler. Disposable module 2 further includes a cannula coupler or port coupler.

FIG. 2c shows a further perspective view of exemplary injection device 1 with cap 13 being removed. Injection Cannula 400 may be a standard cannula as generally known from hand-held-injection devices of the pen type. Injection cannula 400 may include a skin piercing member 405 with a sharpened tip. Skin piercing member 405 is typically made of medical-grade stainless steel but may also be made from medical-grade plastics, further metal alloys, etc. Skin piercing member 400 is an elongated hollow structure, including a conduit that is fluidically coupled with dosing unit outlet 220. Injection cannula 400 further includes a device coupler 410 for coupling injection cannula 400 with injection device 1. Device coupler 410 is typically made from plastic and designed to couple with a cannula coupler of injection device 1 via snap-fit, bayonet, screwed engagement, or the like.

Reusable module 3 and disposable module 2 are designed for a releasable snap-fit. One or multiple release buttons 30 are provided which need to be pressed by a user for separating reusable module and disposable module. FIG. 2c further shows a battery cover 22 that covers a rechargeable or non-rechargeable battery which serves as primary power supply for injection device 1. In dependence of the power supply and the power consumption, a power supply may alternatively be included in disposable module 2.

FIG. 3 shows a schematic perspective view exemplary injection device 1 in a cut-away view with attached injection cannula 400. Disposable frame 26 is arranged inside disposable housing 25 or is formed integral with disposable housing 25. Disposable frame 26 includes cartridge support structure 26a and dosing unit support structure 26b, such that cartridge 100 with cartridge longitudinal axis A' and dosing unit 200 (largely hidden under disposable carrier 26, indicated by dosing unit longitudinal axis A') are, in the assembled state, in a parallel side-by-side arrangement.

Cartridge 100 may be provided readily assembled into cartridge support structure 26a or may be provided separately and assembled by the device user. Disposable housing 25 with disposable support structure 26, reservoir 100 and dosing unit 200 forms a compact disposable module 2 that may be coupled to reusable module 3 as discussed above and discarded at the end of its useful lifetime.

Alternatively, drug reservoir 100 may be a flexible pouch-like or a semi-flexible reservoir. In further variants, either or both of drug reservoir 100 and/or dosing unit 200 may be formed integral with disposable frame 26, e.g. as injection-molded plastic component. In a further variant, those components may be, fully or partly, integral with disposable housing 25 and disposable frame 26 may be omitted. FIG. 3 further shows drive unit 300 in-line with dosing unit 200. Drive unit 300 is based on an electric DC motor as actuator and an attached multi-step planetary gear.

An optic rotational encoder disc 315 is coupled to a rear end of a motor shaft of drive unit 300. The encoder discs forms, in combination with a light barrier arrangement (not shown) an optical encoder for supervising and/or controlling operation of drive 300. Alternatively, the encoder may be based on a different principle and be realized, e.g., as magnetic encoder. An additional or alternative encoder may be partly integral with dosing unit 200 as will be discussed below.

A test strip reception unit 610 is provided that is aligned with test strip port 605 and includes corresponding contacts in case of an electrochemical blood glucose measuring device or optical transmitter and receiver in case of an opto-chemical blood glucose measuring device.

FIG. 3 further shows a power supply 700 in form of a LiPo rechargeable battery, which may alternatively be realized as rechargeable battery of different electro-chemical design, as non-rechargeable battery, or high-energy condenser. In case of a rechargeable battery, it may be reloaded inside and/or outside injection device 1. Power supply 700 powers all electrically powered components of device 1. Power supply 700 is aligned with and is removable via battery cover 22.

Figure 4:
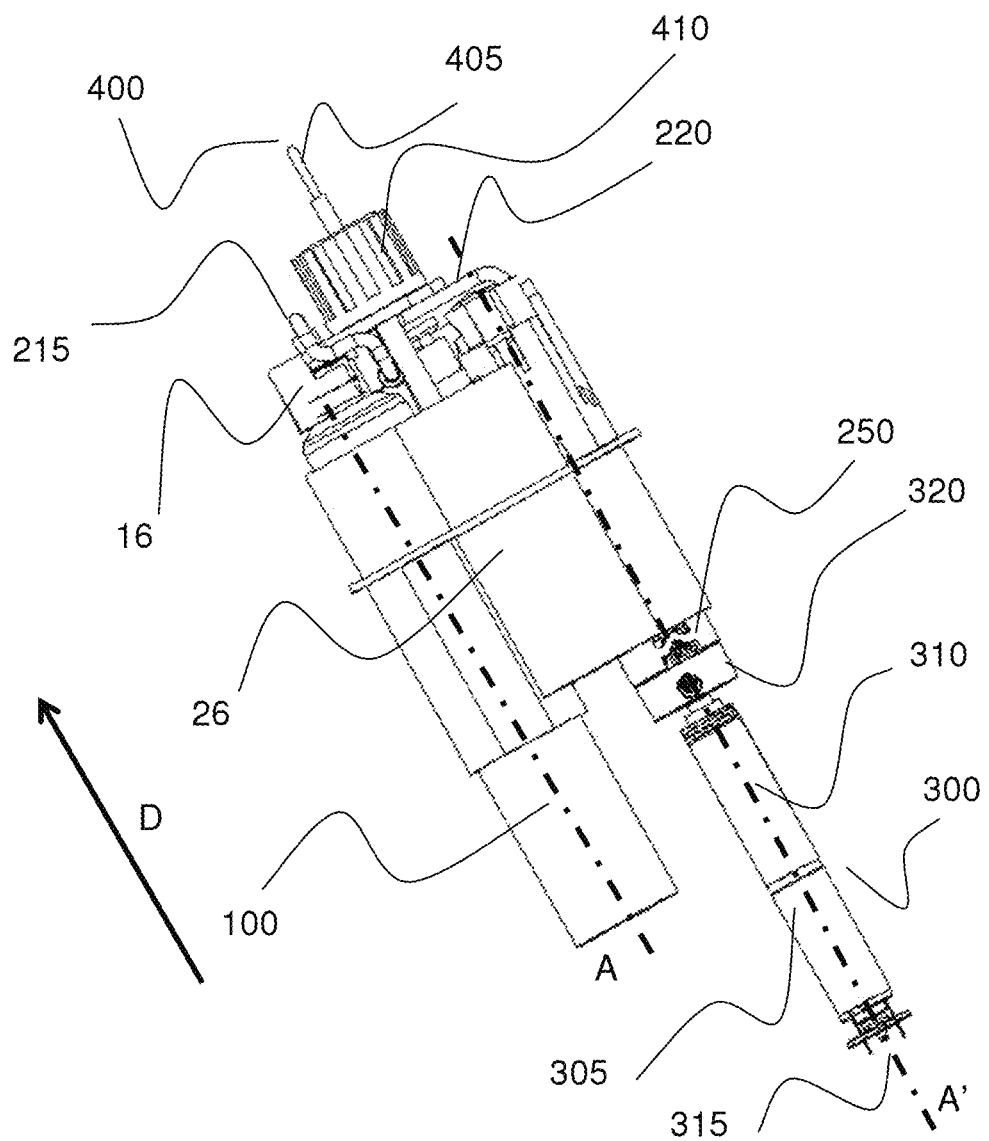
FIG. 4 shows an injection device in a schematic perspective cut-away view, according to at least one embodiment of the present disclosure.

FIG. 4 shows hand-held injection device 1 with attached injection cannula 400 in a cut-away top view. Drive 300 exemplarily is realized by electric motor 305 in-line with and directly attached to gearbox 310, exemplarily realized as multi-stage planetary reduction gear. Reusable drive coupler 320 is coupled to the output side of gearbox 310 and arranged in-line with motor 305 and gearbox 310. Reusable drive coupler 320 forms part of a rotatory drive coupler for transmitting a drive torque from drive unit 300 to dosing unit 200. Reusable drive coupler 320 interacts with disposable drive coupler 250 in form of a jaw teeth clutch or the like. Coupling of reusable drive coupler 320 and disposable drive coupler 250 is achieved by displacing module 3 with reusable drive coupler 320 in direction D relative to disposable module 2 with disposable drive coupler 250. Decoupling is achieved by displacement in the opposite direction. In this way, coupling and decoupling reusable module 3 and disposable module 2 simultaneously couples or decouples drive 300 and dosing unit 200.

FIG. 4 further shows elastic collar 16 as part of the disposable module. Elastic collar 16 holds and secures a distal end section of cartridge 100 via snap fit. A piercing cannula (not visible) is provided in the center of collar 16 to pierce a septum that is provided at a distal from surface of cartridge 100. Collar 16 may be designed for a releasable snap-fit, thus allowing cartridge 100 to be separated after emptying and to be discarded separately. Alternatively, collar 16, once having engaged with cartridge 100, does not allow removal of cartridge 100.

Dosing unit inlet conduit 215 fluidically couples the piercing cannula with the dosing unit inlet. Similarly, dosing unit outlet conduit 220 fluidically couples the dosing unit outlet with skin piercing member 420 of injection cannula 400. Conduits 415, 420 may be realized as dedicated components, e.g. as flexible or rigid tubing, or may, fully or partly, be realized integral with further components of the disposable module, e.g. disposable frame 26.

Figure 5:
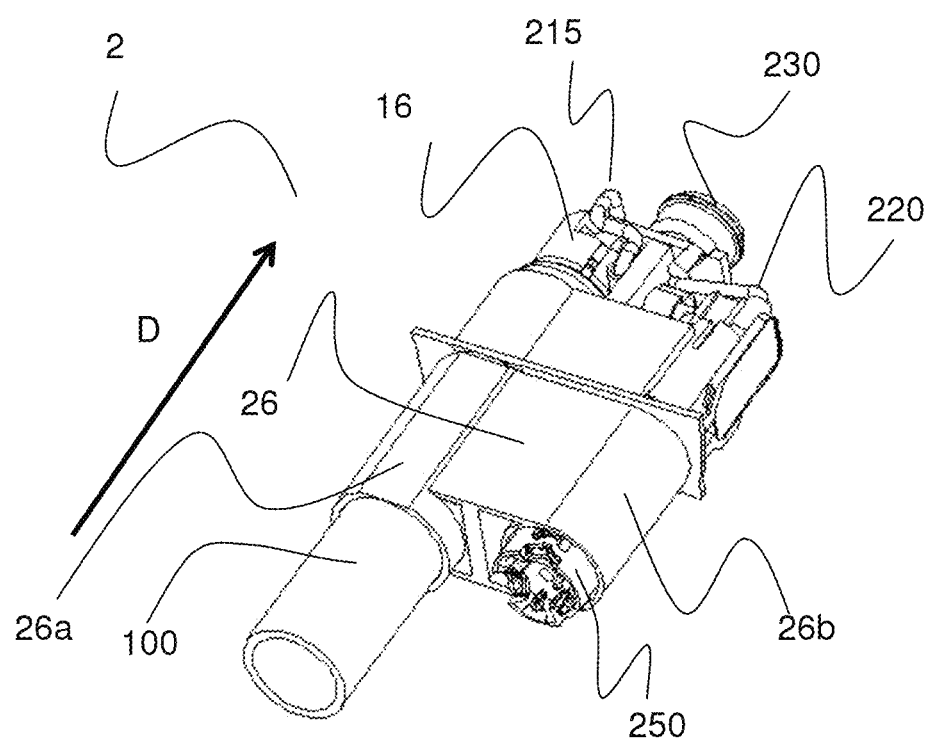
FIG. 5 shows an injection device in a schematic cut-away view, according to at least one embodiment of the present disclosure.

FIG. 5 shows an exemplary embodiment of disposable module 2 with disposable housing 25 being removed in a schematic perspective view. Cannula coupler 230 is designed to releasably couple with device coupler 405 of injection cannula 400 as discussed above.

Figure 6A:
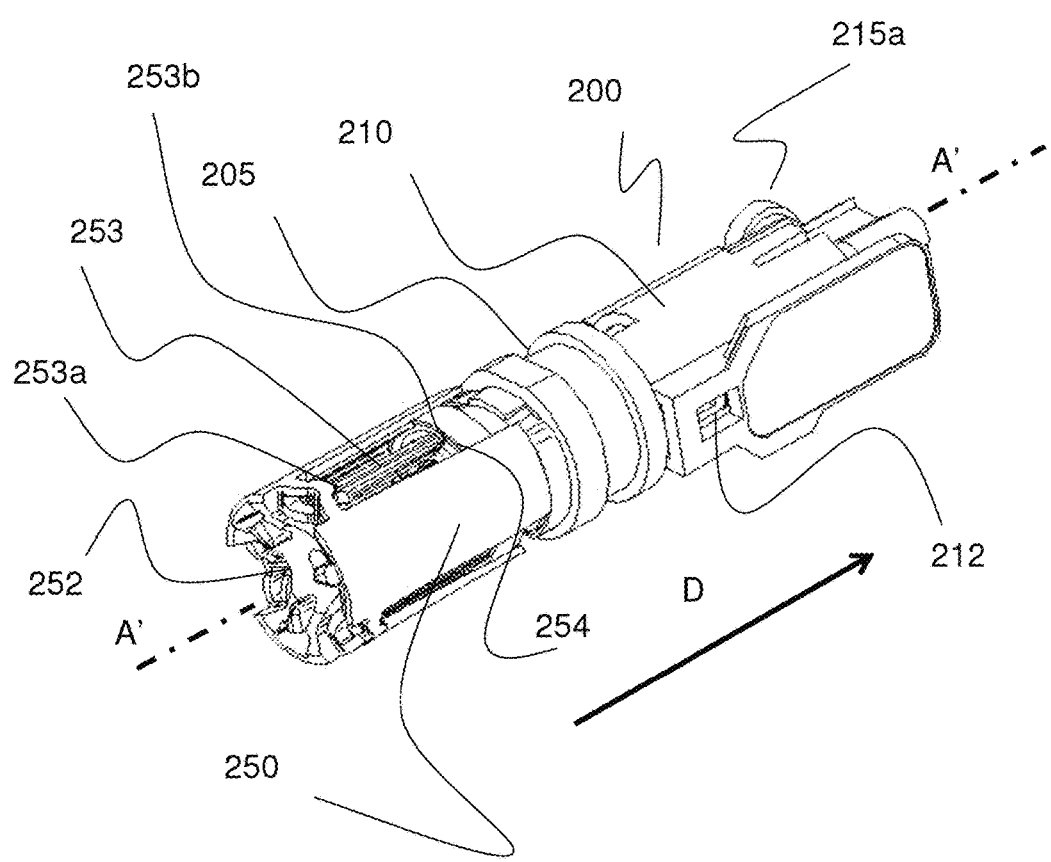
FIGS. 6A and 6B show an exemplary dosing unit in a schematic perspective view, according to at least one embodiment of the present disclosure.
Figure 6B:
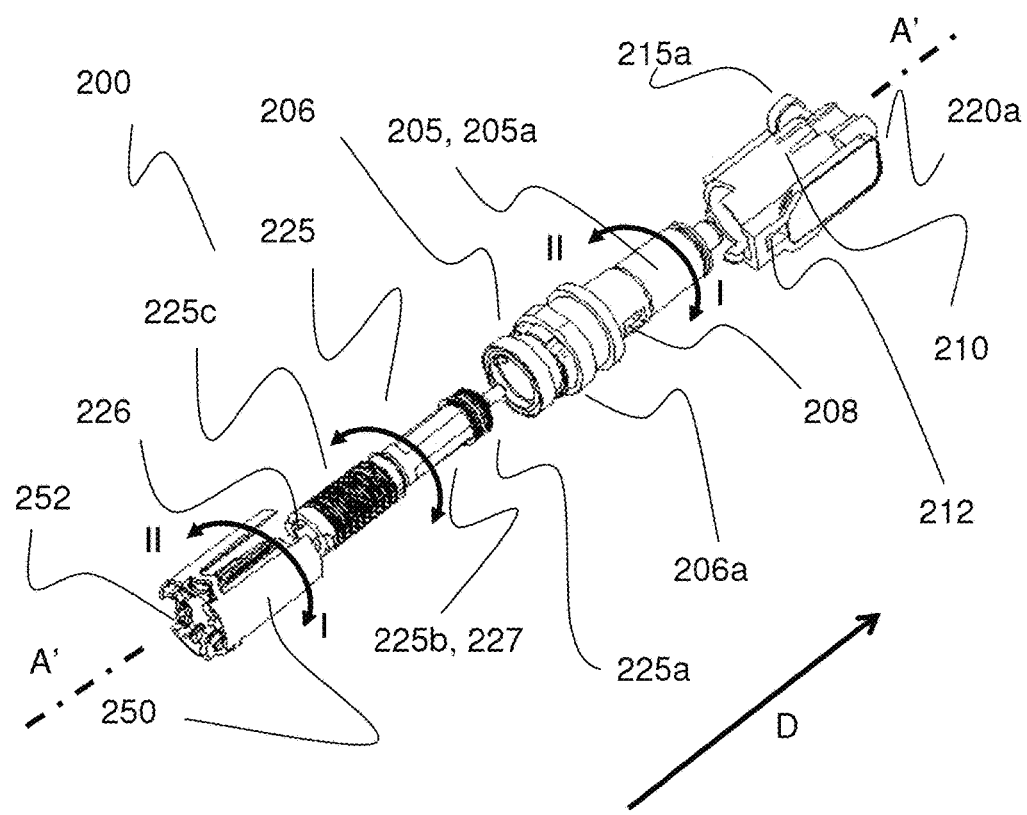

FIG. 6a and FIG. 6b show an exemplary dosing unit 200 in accordance with the present disclosure in an assembled view and an exploded view, respectively.

Exemplary movable member 205 has an elongated tubular shape, the hollow inner volume of movable member 205 forming the metering cavity 207 (not referenced in FIG. 6, see FIG. 1). Movable member 205 is pivotably supported by elongated tubular stationary member 210 which serves as rotatory bearing for movable member 205. At its proximal end section, movable member 205 has a metering cavity aperture which may, in dependence of its rotational position with respect to stationary member 210, be aligned with dosing unit inlet 215a with dosing unit outlet 220a, or with neither of them. If the metering cavity aperture is aligned with dosing unit inlet 215a, dosing unit 200 is in the inlet state. If the metering cavity aperture is aligned with dosing unit outlet 220a, dosing unit 200 is in the outlet state. The metering cavity aperture is temporary not aligned with either of dosing unit inlet 215a or dousing unit outlet 220 when switching between inlet state and outlet state. In this intermediate state, the metering cavity is fluidically isolated. In some embodiments, however, a venting aperture (not visible) is provided in stationary member 210 in fluidic communication with the environment such that the metering cavity aperture passes the venting aperture when switching between inlet state and outlet state. In such embodiments, any differential fluidic pressure that may have built up inside metering cavity 207 with respect to the environment, e.g. resulting from a temperature change, is equalized each time dosing unit 200 is switched between inlet state and outlet state.

An arrangement of stops (not visible) is provided at movable member 205 and stationary member 210. Those stops define two rotational end positions of movable member 205 with respect to stationary member 210. One of the end positions results in the valve arrangement being in the inlet state, the other end position results in the valve arrangement being in the outlet state. The rotational angle of movable member 205 is favorably limited by the stops to an angle less than a full rotation, e.g. 60°, 120° or 180°. Inside of hollow cylindrical metering cavity 207, piston 225 is arranged in a telescopic and co-axial arrangement, such that the cylinder axis of metering cavity 207 coincides with the axis of rotation of movable member 205 with respect to stationary member 210.

Piston 225 includes sealing distal piston end section 225a. Sealing against an inner surface of the metering cavity may be achieved by sealing lips that are integral with piston 225 and manufactured, e.g., in a two-component injection molding process with piston 225 generally made from hard plastics and the sealing lips from soft plastics. Alternatively, dedicated separate sealing elements, such as O-rings, may be used or distal piston end section 225a and metering cavity 207 may be designed to for a hard-hard sealing. Piston 225 further included a piston shaft 225b, 225c, the piston shaft extending in proximal direction from distal piston end section 225a. The piston shaft includes an elongated piston middle section 225b and an elongated threaded proximal piston end section 225c, proximal piston end section 225c having an outside thread. A corresponding threaded element 206 is provided to the proximal end of movable member 205, threaded element 206 having an inside thread and engaging, in the assembled state, proximal piston end section 225c. Piston 225 may be displaced in proximal direction, against direction D, and in distal direction, as indicated by direction D. in a screw-like way without movement of the movable member 205. The total travel distance of piston 225 is limited between a proximal end position and a distal end position. In the distal end position, the drug-filled active volume of metering cavity is substantially zero and all or most of the length of piston 225 is received inside movable member 225. In the proximal end position, the drug-filled active volume of metering cavity 207 is minimal. Here, sealing distal piston end section 225a is seated in a most distal area of metering cavity 207 with proximal piston end section 225c largely projecting out of movable member 225.

A minimum length for both piston middle section 225b and proximal piston end section 225c is given by the total travel distance of piston 225 between proximal end position and distal end position, respectively.

Piston 225 may further rotate or pivot together with movable member 205 with respect to stationary member 210 synchronously, that is, without relative motion between movable member 205 and piston 225. Combined rotation of movable member 205 and piston 225 occurs when switching the valve arrangement between inlet state and outlet state, respectively. Prevention of any relative motion, in particular of any displacement of piston 225 with respect to movable member 205 results in the valve switching not resulting in a dosing error because the drug-filled active volume 207a of metering cavity 207 does not change.

Threaded element 206 may be provided as dedicated element and rigidly attached, e.g. by clamping or gluing, to movable member 205. Alternatively, threaded element 206 may be formed integral with movable member 205 in an injection molding process. The symmetry axis of threaded element 206 is coaxial with the cylinder axis of metering cavity 207. Threaded element 206 is accordingly arranged coaxial with and proximal of metering cavity 207.

Optional play removal clamp 206a is clipped onto or otherwise attached to threaded element 206 and exerts a radial biasing force onto the threaded engagement, thus ensuring play-free engagement of movable member 205 and piston 225. Play free engagement is advantageous because any play that would result in a some amount of free and controlled displacement potentially occurring between piston 225 and movable member 205, resulting in a corresponding change in the drug-filled active volume of metering cavity 207. Alternatively to play removal clamp 206a, other biasing devices, such as a linear spring or a leaf spring, may be used for exerting a radial and/or axial biasing force onto the threaded engagement. Providing a play removal device made from metal is considered favorable as it less susceptible to aging and environmental impact factors such as humidity or temperature, as compared to typical (thermo) plastic materials. However a play removal device may also be formed form plastics or further materials, such as compound materials. Furthermore, a play removal device may be integral with threaded element 206 and/or threaded proximal piston end section 225c, e.g. by exploiting material-inherent elasticity.

Piston 225 is realized as generally hollow structure with tubular piston cavity 226, piston cavity 226 extending into an aperture at the proximal end surface of piston 225, in particular of proximal piston end section 225c. Piston cavity 226 may have a non-circular cross section, such as an oval, triangular, quadratic, hexagonal cross section. Alternatively, piston cavity 226 may have a generally circular cross section with one or multiple radial protrusions, dents, or cut-ins.

Disposable drive coupler 250 may be formed by a generally hollow structure with an open distal front surface, thus allowing disposable drive coupler 250 to receive proximal piston end section 225c in a telescopic and co-axial way. An elongated drive pin (not visible in FIG. 6a, 6b) is provided inside and along the center line of disposable drive coupler 250, the drive pin being shaped to engage with piston cavity 226 in a sliding engagement with favorably little or virtually no rotational play, thus allowing transmitting a driving torque onto plunger 225 without linear force transmission.

Furthermore, disposable drive coupler 250 and movable member 205 in at least one embodiment are designed for a sliding rotational and coaxial engagement with little or virtually no axial play such that disposable drive coupler 250 is free to rotate with respect to movable member 205 about axis A'. That is, disposable drive coupler 250 may rotate but has a fixed axial position with respect to movable member 205.

Disposable drive coupler 250 further includes drive engagement structure 252 for rotational coupling to reusable drive coupler 320. Engagement structure 252 includes an arrangement of pawls or teeth (not referenced)) for the torque transmission.

General operation of dosing unit 200 in at least one embodiment is as follows: When rotating disposable drive coupler 250 (via drive unit 200) in a rotational distal driving direction I, a rotational motion is transmitted via the drive pin inside disposable drive coupler 250 and piston cavity 226 onto piston 225, thus resulting in a screw-like displacement of piston 225 in distal direction D, and decreasing the liquid filled active volume of the metering cavity. This requires dosing unit 200 to be in its outlet state, thus enabling a displacement of drug out of metering cavity 207 into dosing unit outlet 220a. Plunger 225 is displaced in a single or number of consecutive injections until it assumes its distal end position.

Since, in the distal end position, plunger 225 is fully or largely positioned inside the hollow structure of movable member 205, the drive pin of disposable drive coupler 250 and piston cavity 226 of piston 225 are designed and arranged such that correct engagement for torque transmission is ensured in the distal end position of piston 225.

By a rotation of disposable drive coupler 250 in the opposite proximal driving direction II, piston 225 carries out a screw-like displacement movement in proximal direction against direction D, thus increasing the drug-filled active volume of the metering cavity. This requires dosing unit 200 to be in the inlet state, such that drug can be drawn into the metering cavity via dosing unit inlet 215a.

For switching the valve arrangement between inlet state and outlet state, a driving torque is transmitted onto movable member 205. The required driving torque may be transmitted by frictional coupling of the fluidic sealing via distal piston end section 225a and/or via the threaded engagement 206, 225c. In dependence of those frictions as compared to a friction between movable member 205 and stationary member 210, dosing unit 200 may be designed such that a rotation of disposable drive coupler 250 generally results in a screw-like displacement of piston 225 in proximal or distal direction, respectively. If, however, piston 225 is in its most distal or most proximal position further piston displacement is impossible due to the limited travel distance. A further rotational motion of disposable drive coupler 250 in the same direction is transmitted, via piston 225, onto movable member 205, thus resulting in piston 225 and movable member 205 to rotate together and synchronously without relative motion, thus switching the valve state. The combined motion of piston 225 and movable member 205 ends when further rotation of movable member 205 is blocked by the arrangement of stops as discussed above. In such an arrangement, switching the valve is only possible in the most proximal and most distal position of piston 225.

Alternatively, dosing unit 220 may be designed such that a rotation of disposable drive coupler 250 first results in movable member 205 and piston 225 to rotate together and synchronously without relative motion until further rotation of movable member 205 is blocked by the arrangement of stops with the valve arrangement being in the inlet state or outlet state, respectively. Further, rotation of disposable drive coupler 252 in the same direction results in a screw-like displacement of plunger 225 in proximal or distal direction, respectively. This kind of design allows switching between inlet state and outlet state for any piston by changing the rotational direction of the drive. With respect to further discussions of the relation between piston displacement and valve switching, reference is made to application EP 2163273A1.

In the embodiment of dosing unit 200 as shown in FIG. 6, further optional measures are provided for valve switching. Disposable drive coupler 250 includes elongated pivoting pin 253. Pivoting pin 253 is fixed at a proximal end by means of an elastic pivoting hinge 253a, such as an integral hinge or film hinge. Pivoting hinge 253a allows pivoting pin 253 to pivot about an axis perpendicular to longitudinal dosing unit axis A'. A pivoting pin distal end 253b is symmetrically chamfered, thus forming a tip. Pivoting pin distal end 253b is in sliding engagement with a corresponding sliding surface 254 of movable member 205 or threaded element 206, respectively.

Pivoting pin 253 has a length that is slightly greater than a distance between pivoting hinge 253a and sliding surface 254, resulting in pivoting pin 253 being somewhat pivoted and misaligned, i.e., non-parallel, with respect to longitudinal dosing unit axis A'. During normal operation, the additional sliding friction between pivoting pin distal end 253b and sliding surface 254 is low or negligible.

Whenever the rotational movement of disposable drive coupler 250 is changed, however, the engagement of chamfered pivoting pin distal end 253b and sliding surface 254 results in pivoting pin 253 to pivot, via an intermediate state where pivoting pin 253 is aligned with longitudinal dosing unit axis A', into an opposite misaligned configuration. This pivoting motion is associated with a frictional force peak between pivoting pin distal end 253b and sliding surface 254. The frictional force peak results, via pivoting pin 253 and sliding surface 254, in a temporary direct coupling of disposable drive coupler 2520 and movable member 205.

By the arrangement of FIG. 6, the valve state of dosing unit 200 may accordingly be switched in a defined and reliable way for any position of piston 225 by reversing the driving direction, even if the frictional forces between movable member 205 and piston 225 are varying or somewhat undefined.

While only one pivoting pin 253 is shown in FIG. 6, a number of two, three or more pivoting pins 253 may be present that are distributed about the circumference of disposable drive coupler 250. Alternatively to the arrangement as shown in FIG. 6, further selective coupling arrangements, such as a wrap spring clutch or selective clamping of the threaded engagement 206, 225c may be used, as disclosed in application EP 2163273A1.

FIG. 6b further shows an optional encoder scale 227 on piston middle section 225b. Encoder scale 227 is realized by a pattern of longitudinal stripes of different optical properties, such as alternating light and dark stripes. Ambulatory infusion device 1 may include an optical sensor, such as a reflection light barrier that is arranged at a fixed position to scan the light reflected by encoder scale 227, thus generating binary and alternating electric signal resulting from a rotational motion of piston 225. Providing such an encoder additionally or alternatively to an encoder of the drive unit 300 (encoder disc 315 in FIG. 3, 4) has the advantage of the encoder signal being related to the actual piston displacement, thus avoiding failures or uncertainties that may generally result, e.g., from mechanical play in the drive coupling. Furthermore, it is more reliable since in case, e.g. of a system fault such as a broken disposable drive coupler 250 that may cause piston 225 not to be displaced even though motor 305 is activated and running.

In the embodiment shown in FIG. 6, further optional measures are taken to confirm successful valve switching. Encoder scale 227 is arranged such that it is not directly optically accessible for an optical sensor, but only via movable member windows 208 and stationary member window 212. The optical sensor is aligned with stationary member window 212. A pair of movable member windows 208 (with only one being visible in FIG. 6) is arranged such that one of the movable member windows 208 is aligned with the stationary member window 212 for the rotational position of movable member 205 corresponding to the inlet state and the other movable member window 208 is aligned with stationary member window 212 for the rotational position of movable member 205 corresponding to the outlet state. For an intermediate rotational position of movable member 205, as occurring during the valve switching process, encoder scale 227 is covered by the generally opaque body of movable member 205, resulting in no reflected light being received by the optical sensor as plunger 225 moves. In this way, successful valve switching can be confirmed. It should be noted that stationary member window 212 may be omitted if stationary member 212 is designed such that movable member window 208 is not covered by stationary member 210. Furthermore, a similar encoder may be based on a different sensing principle and be realized, e.g., as galvanic electrical encoder or magnetic encoder.

A dosing unit as shown in FIG. 6 may be varied in a number of ways. For example, features and elements such as disposable drive coupler 225, encoder scale 227 and windows 208, 212 and play reduction device 206 a may be omitted or realized in a different way.

Figure 7A:
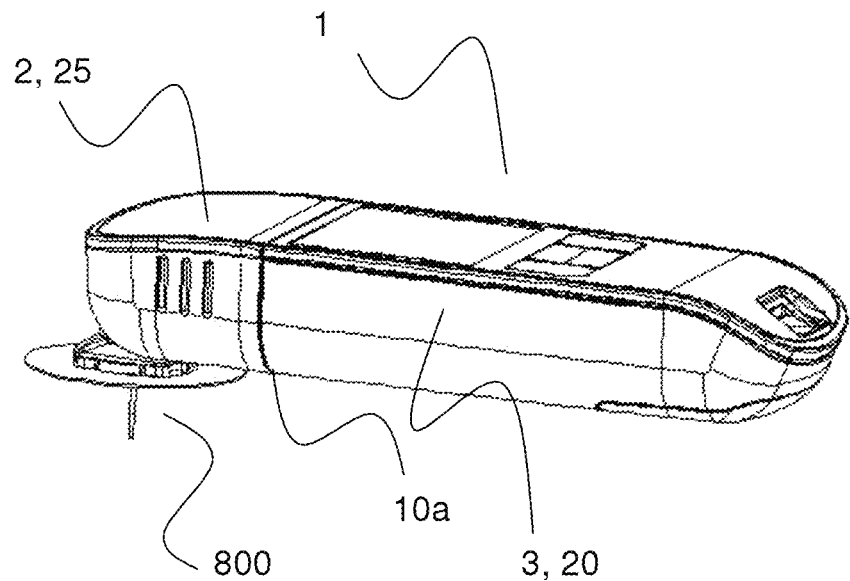
FIGS. 7A-7C show an exemplary injection device in a schematic perspective view, according to at least one embodiment of the present disclosure.
Figure 7B:
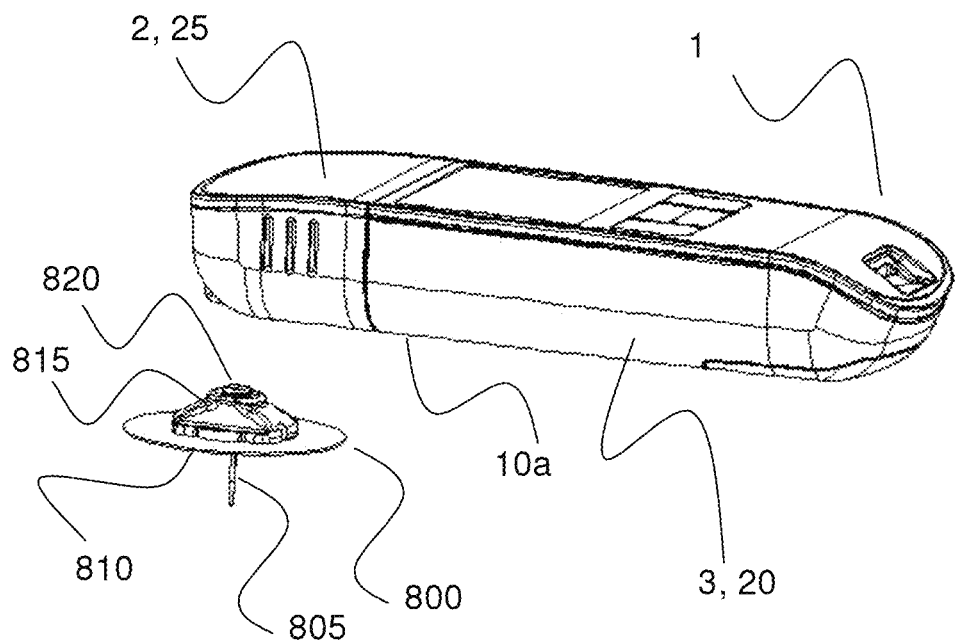
Figure 7C:
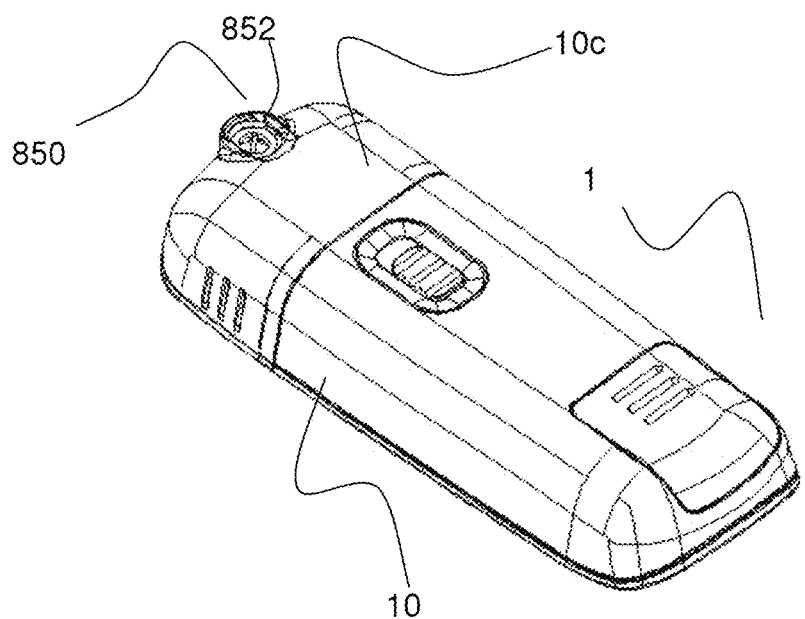
Figure 8:
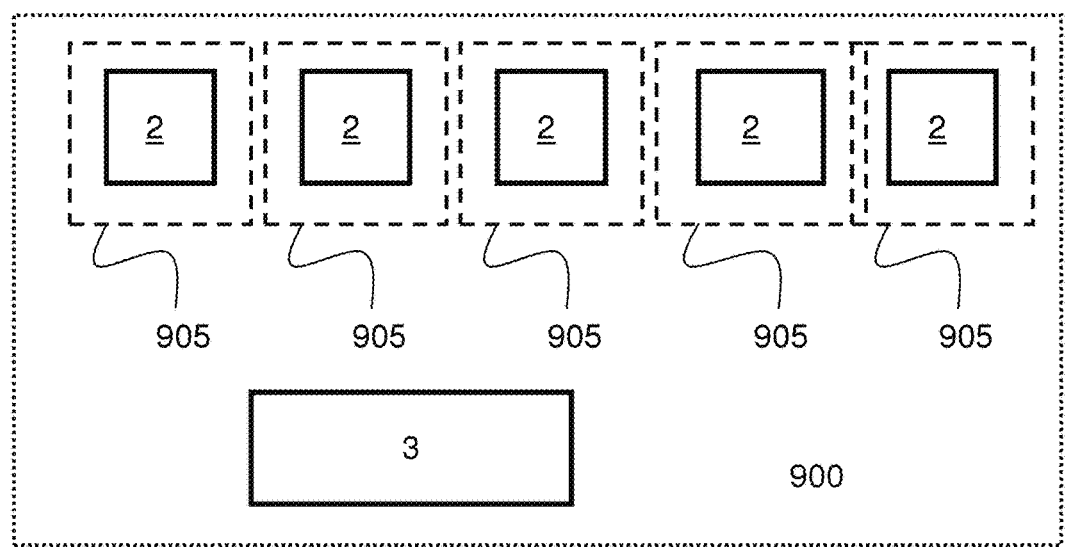
FIG. 8 schematically shows an injection device kit, according to at least one embodiment of the present disclosure.

FIG. 7a to FIG. 7c show a further exemplary embodiment of hand-held injection device 1 in different schematic perspective views. In this embodiment, injection device 1 is configured to couple to a subcutaneous port 800. FIG. 7a shows injections device 1 coupled to subcutaneous port 800.

FIG. 7b show injection device 1 and port 800 in a decoupled view. FIG. 7c shows a bottom view of injection device 1 with port coupler 825.

Port 800 may include a subcutaneous port cannula 805 that may be made of a soft material, such as Teflon, or of a hard material, such as medical-grade plastics or stainless steel. During application of port 800, subcutaneous port cannula 805 is seated in a user's subcutaneous tissue. Subcutaneous port cannula 805 is in fluidic communication with a receiving cavity (not referenced) which is formed inside a extracorporeal port housing 815. Port housing 815 is attached to the user's skin via adhesive pad 810 for an application time of typically some days.

Port coupler 850 is provided on housing bottom surface 10a of device housing 10 and includes a mating structure (not referenced) that is designed to temporarily and releasably mate with a device coupler structure of port housing 815. Port coupler 850 further includes a short port coupler cannula 852 for piercing port septum 820, port septum 820 sealing the receiving cavity of port 800. For carrying out an injection, a user temporarily couples injection device 1 with port 800.

Besides port coupler 850, injection device 1 as shown in FIG. 7 may be designed in the same way and offer the same features and design variants as discussed above. Injection device 1 may further be designed as modular device that may be used in combination with a subcutaneous cannula 400 or a subcutaneous port 800, with most of the components, such as drive unit, circuitry, power supply, or blood glucose measurement device being maintained. In a variant of injection device 1 as shown in FIG. 7, a cannula coupler may be may be provided in addition or alternatively to port coupler 850.

FIG. 9 shows an exemplary injection device kit 900 in a schematic and structural view. Injection device kit 900 includes a reusable module 3 and a number of disposable modules 2 as disused above. Each disposable module 2 is favorably provided as hermetically sealed in an individual sterile package 905.

Such an injection device kit has the advantage that reusable module 3 can be used in combination with a number of disposable modules 2 in sequence and does accordingly not need to be discarded together with each disposable module 2. However, providing a new reusable module 3 from time to time prevents components of disposable module 3, such as drive unit, to wear out to a degree where safe operation and/or the dosing accuracy may be adversely affected. Furthermore, a device user can always be supplied with a most up-to-date version of reusable module 3.

Optionally, each disposable module may include coding means, such as a bar code or an RFID tag that carries information such as a production lot number and/or an expiry date. Reusable module 3 may include a corresponding data reader to read the information from the coding means. Operation may, for example not be possible if an expiry date of a disposable unit 2 has exceeded. Additionally or alternatively, the reusable module 3 and the number of disposable modules 2 that are commonly provided as injection device kit may be paired by the coding means of the disposable modules 2 and the reusable module 2 storing a common kit identifier, lot identifier or the like. Operation may be prevented if the information stored by disposable module 2 and reusable module 3 does not match.

While various embodiments of hand-held devices and methods for using the hand-held devices have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

The invention claimed is:

1. A hand-held injection device for the metered injection of a liquid drug into a person's tissue, the injection device comprising:

a housing, the housing being sized and shaped to be grasped by a user with a single hand for carrying out an injection;

an elongated drug reservoir having a longitudinal reservoir axis (A);

an elongated dosing unit having a dosing unit inlet, a dosing unit outlet, and a metering cavity, the dosing unit having a longitudinal dosing unit axis (A'), the drug reservoir being fluidically coupled to the dosing unit inlet;

wherein the dosing unit and the drug reservoir are arranged such that the longitudinal dosing unit axis (A') is in parallel alignment with the reservoir axis (A);

wherein the dosing unit is structured to allow the flow of the liquid drug from the drug reservoir into the metering cavity via the dosing unit inlet, thus charging the metering cavity, and to subsequently discharge the metering cavity by dosing drug out of the metering cavity into the dosing unit outlet;

wherein the dosing unit includes a drive coupler for coupling the dosing unit for an application time of the dosing unit to an actuator, such that operation of the actuator results in the metering cavity being charged or discharged, respectively; and wherein the dosing unit includes a valve arrangement, and wherein the valve arrangement is configured to be switchable between an inlet state and an outlet state, such that in the inlet state, the dosing unit inlet is fluidically coupled to the metering cavity and the dosing unit outlet is fluidically separated from the metering cavity, and such that in the outlet state, the metering cavity is fluidically coupled with the dosing unit outlet and the dosing unit inlet is fluidically separated from the metering cavity, wherein there is no state of the valve arrangement where both the dosing unit inlet and the dosing unit outlet are fluidically coupled with the metering cavity.

2. The hand-held injection device of claim 1, wherein the hand-held injection device is structured, subsequent to charging the metering cavity, to stepwise discharge the metering cavity in a number of separate injections.

3. The hand-held injection device of claim 1, further comprising a user-operated dose setting control, the user-operated dose setting control being coupled to the dosing unit for setting an individual dose volume for each injection.

4. The hand-held injection device of claim 1, wherein the elongated dosing unit includes a stationary member and a movable member, the movable member includes a dosing cavity, wherein the movable member and the stationary member, in combination, form the valve arrangement such that a relative motion of the movable member with respect to the stationary member switches the valve arrangement between the inlet state and the outlet state.

5. The hand-held injection device of claim 1, wherein the dosing unit includes a piston pump, the piston pump including a piston, the piston being linearly displaceable in the metering cavity between a proximal end position and a distal end position for charging and discharging the metering cavity.

6. The hand-held injection device of claim 5, wherein the piston includes an encoder scale.

7. The hand-held injection device of claim 1, wherein the drive coupler is structured to couple to a single actuator for switching the valve arrangement between the inlet state and the outlet state and alternatively charging and discharging the metering cavity.

8. The hand-held injection device of claim 7, wherein the dosing unit includes a piston pump, the piston pump including a piston, the piston being linearly displaceable in the metering cavity between a proximal end position and a distal end position for charging and discharging the metering cavity, wherein the dosing unit is designed to couple the piston for an application time of the dosing unit, continuously to the actuator and to selectively frictionally couple a movable member to the actuator for switching the valve arrangement between the inlet state and the outlet state.

9. The hand-held injection device of claim 8, wherein the selective frictional coupling of the movable member to the actuator is independent from the coupling of the piston to the actuator.

10. The hand-held injection device of claim 1, further comprising a drive unit, the drive unit including a single actuator.

11. The hand-held injection device of claim 10, wherein the single actuator is an electric motor and the hand-held injection device further includes control circuitry, the control circuitry being operatively coupled to the electric motor.

12. The hand-held injection device of claim 10, wherein the drive unit has a longitudinal drive unit axis, the longitudinal drive unit axis being in-line with or parallel to the longitudinal dosing unit axis (A').

13. The hand-held injection device of claim 1, further including a biasing device, the biasing device pressurizing the drug inside the drug reservoir.

14. The hand-held injection device of claim 1, further comprising a cannula coupler or a port coupler, releasably mechanically coupling the hand-held injection device to an injection cannula or a subcutaneous port and structured to releasably fluidically couple the dosing unit outlet with the injection cannula or the subcutaneous port.

15. The hand-held injection device of claim 14, wherein the cannula coupler or the port coupler is arranged to couple the hand-held injection device and the injection cannula or the subcutaneous port such that the longitudinal reservoir axis (A) is perpendicular to longitudinal cannula axis or port axis.

16. The hand-held injection device of claim 1, further comprising a user-operable reservoir coupler.

17. The hand-held injection device of claim 1, further including a measurement device, the measurement device operable to determine a presence and/or a concentration of an analyte within a human's blood.

18. The hand-held injection device of claim 1, further comprising a disposable module, the disposable module including the dosing unit, the hand-held injection device further including a reusable module, the reusable module including circuitry, wherein the disposable module and the reusable module are designed to releasably couple such that the disposable module is disposable by a device user with the reusable module being maintained for subsequently coupling with a further disposable module.

19. An injection device kit, the injection device kit comprising:
   a disposable module comprising the hand-held injection device of claim 1; and
   a reusable module comprising circuitry and a drive unit;
   wherein the reusable module and the disposable module are structured to be coupled together by a user.

* * * * *